United States Patent
Putman et al.

(10) Patent No.: US 10,146,041 B1
(45) Date of Patent: Dec. 4, 2018

(54) SYSTEMS, DEVICES AND METHODS FOR AUTOMATIC MICROSCOPE FOCUS

(71) Applicant: Nanotronics Imaging, Inc., Cuyahoga Falls, OH (US)

(72) Inventors: John B. Putman, Celebration, FL (US); Matthew C. Putman, Brooklyn, NY (US); Vadim Pinskiy, Wayne, NJ (US); Denis Y. Sharoukhov, Brooklyn, NY (US)

(73) Assignee: Nanotronics Imaging, Inc., Cuyahoga Falls, OH (US)

( * ) Notice: Subject to any disclaimer, the term of this patent is extended or adjusted under 35 U.S.C. 154(b) by 0 days.

(21) Appl. No.: 15/967,802

(22) Filed: May 1, 2018

(51) Int. Cl.
| | |
|---|---|
| *G02B 21/24* | (2006.01) |
| *G02B 21/00* | (2006.01) |
| *G02B 21/36* | (2006.01) |
| *H04N 5/232* | (2006.01) |
| *G02B 7/38* | (2006.01) |
| *G01N 15/14* | (2006.01) |
| *H04N 5/225* | (2006.01) |

(52) U.S. Cl.
CPC ......... *G02B 21/244* (2013.01); *G01N 15/147* (2013.01); *G02B 7/38* (2013.01); *G02B 21/002* (2013.01); *G02B 21/242* (2013.01); *G02B 21/365* (2013.01); *H04N 5/2258* (2013.01); *H04N 5/23212* (2013.01)

(58) Field of Classification Search
CPC ...... G02B 21/244; G02B 7/38; G02B 21/242; G02B 21/002; G02B 21/365; H04N 5/23212; H04N 5/2258; G01N 15/147
See application file for complete search history.

(56) References Cited

U.S. PATENT DOCUMENTS

| | | | |
|---|---|---|---|
| 4,661,692 | A | 4/1987 | Kawasaki |
| 4,945,220 | A | 7/1990 | Mallory et al. |
| 5,604,344 | A | 2/1997 | Finarov |
| 5,973,846 | A | 10/1999 | McConica |
| 6,043,475 | A | 3/2000 | Shimada et al. |
| 6,160,607 | A | 12/2000 | Diaconu |
| 6,795,172 | B2 | 9/2004 | Putman et al. |
| 6,879,440 | B2 | 4/2005 | Cemic et al. |
| 7,345,814 | B2 | 3/2008 | Yoneyama et al. |

(Continued)

FOREIGN PATENT DOCUMENTS

| | | |
|---|---|---|
| DE | 10112639 | 9/2002 |
| JP | 19940209734 | 3/1996 |

(Continued)

OTHER PUBLICATIONS

Chow et al., "Nikon Optical Microscope", Technical Paper, UW Nanomech Lab, Jan. 2009, pp. 1-2.

(Continued)

*Primary Examiner* — Tony Ko
(74) *Attorney, Agent, or Firm* — Byrne Poh LLP

(57) ABSTRACT

An automatic focus system for an optical microscope that facilitates faster focusing by using at least two offset focusing cameras. Each offset focusing camera can be positioned on a different side of an image forming conjugate plane so that their sharpness curves intersect at the image forming conjugate plane. Focus of a specimen can be adjusted by using sharpness values determined from images taken by the offset focusing cameras.

20 Claims, 10 Drawing Sheets

(56) References Cited

U.S. PATENT DOCUMENTS

| | | |
|---|---|---|
| 7,583,380 B2 | 9/2009 | Van Beek et al. |
| 7,772,535 B2 | 8/2010 | Krief et al. |
| 8,174,762 B2 | 5/2012 | Xu et al. |
| 8,576,483 B2 | 11/2013 | Tanabe et al. |
| 9,091,525 B2 | 7/2015 | Sulik et al. |
| 9,207,444 B2 * | 12/2015 | Yamamoto ............... G02B 7/28 |
| 9,488,819 B2 | 11/2016 | Putman et al. |
| 2003/0184856 A1 | 10/2003 | Otaki |
| 2003/0215725 A1 | 11/2003 | Watanabe |
| 2005/0063049 A1 | 3/2005 | Steenblik et al. |
| 2005/0121596 A1 | 6/2005 | Kam et al. |
| 2007/0152130 A1 | 7/2007 | Fomitchov |
| 2008/0219654 A1 | 9/2008 | Border et al. |
| 2009/0225199 A1 | 9/2009 | Ferren |
| 2010/0033811 A1 | 2/2010 | Westphal et al. |
| 2010/0182680 A1 | 7/2010 | Hayashi |
| 2015/0070655 A1 | 3/2015 | Rossi |
| 2016/0216504 A1 | 7/2016 | Hing et al. |
| 2017/0329122 A1 * | 11/2017 | Osawa ................... G02B 21/06 |

FOREIGN PATENT DOCUMENTS

| | | |
|---|---|---|
| JP | 19970363313 | 9/1998 |
| JP | 2012181341 | 9/2012 |
| WO | WO 2014036276 | 3/2014 |

OTHER PUBLICATIONS

Groen et al., "A Comparison of Different Focus Functions for Use in Autofocus Algorithms", in Cytometry, Mar. 1985, pp. 81-91.

Liu et al., "Dynamic Evaluation of Autofocusing for Automated Microscopic Analysis of Blood Smear and Pap", in Journal of Microscopy, vol. 227, pt. 1, Jan. 2007, pp. 15-23.

Marvell Nanofabrication Laboratory, "NanoSpec Film Thickness Measurement System", Lab Manual, University of California, Berkeley, pp. 1-5.

McKeogh et al., "A Low-Cost Automatic Translation and Autofocusing System for a Microscope", in Measurement Science and Technology, vol. 6, No. 5, Jan. 1995, pp. 583-587.

Molecular Expressions, "Optical Microscopy Primer—Anatomy of the Microscope: Kohler Microscope Illumination", publicly available on or before Dec. 26, 2016, pp. 1-10, available at: https://micro.magnet.fsu.edu/primer/anatomy/kohler.html.

Motion X Corporation, "FocusTrac Laser Auto Focus Systems", Technical Paper, retrieved May 7, 2012, pp. 1-3.

Nikon Instruments, "Perfect Focus System", last accessed Mar. 31, 2012, available at http://www.nikoninstruments.com/Information-Center/Perfect-Focus-System-PFS.

Nikon Microscopy U, "Cojugate Planes in Optical Microscopy", last accessed Feb. 27, 2018, available at https://www.microscopyu.com/microscopy-basics/conjugate-planes-in-optical-microscopy.

Nikon Microscopy U, "Depth of Field and Depth of Focus", last accessed May 8, 2012, available at https://www.microscopyu.com/microscopy-basics/depth-of-field-and-depth-of-focus.

Nikon Microscopy U, "Objective Working Distance", last accessed May 8, 2012, available at https://www.microscopyu.com/tutorials/workingdistance.

Nikon Microscopy U, "Properties of Microscope Objective", last accessed May 13, 2012, available at https://www.microscopyu.com/microscopy-basics/properties-of-microscope-objectives.

Nikon Microscopy U, "The Automatic Microscope", last accessed May 7, 2012, available at https://www.microscopyu.com/applications/live-cell-imaging/the-automatic-microscope.

Objective Imaging, "OASIS-AF AutoFocus Module", Technical Paper, 2001, pp. 1-2.

Office Action dated Jul. 30, 2018 in U.S. Appl. No. 15/920,850.

Prior Scientific, "Product Information", last accessed May 7, 2012, available at https://www.prior.com/productinfo_auto_focusoptions.html.

Spencer, "Fundamentals of Light Microscopy: Microscope Alignment", University of Cambridge, 1982, pp. 3-7.

Yazdanfar et al., "Simple and Robust Image-Based Autofocusing for Digital Microscopy", in Optics Express, vol. 16, No. 12, Jun. 9, 2008, pp. 1-8.

* cited by examiner

SYSTEMS, DEVICES AND METHODS FOR AUTOMATIC MICROSCOPE FOCUS

TECHNICAL FIELD

The present disclosure relates to image-based mechanisms for automatic microscope focus.

BACKGROUND

Most specimens that are observed with a microscope have small variations in height across their surfaces. While these variations are frequently not visible to the human eye, they can cause images of a portion of a specimen captured by a microscope to be out of focus.

The range in which a microscope can create a usable focused image is known as the depth of field. The microscope must keep a portion of a specimen within its depth of field to generate useful images. However, when transitioning from observing a first portion of a specimen to observing a second portion of the specimen, the small variations in height of the specimen may cause the second portion to be outside the depth of field.

Different sharpness measurements such as image contrast, resolution, entropy and/or spatial frequency content, among others, can be used to measure the quality of focus of images captured by a microscope. Generally, when a specimen is in focus, the captured image will exhibit the best sharpness quality (e.g., large contrast, a high range of intensity values and sharp edges). The different sharpness measurements that can be used to determine when a specimen is in focus usually require capturing a series of images at different distances between a microscope objective lens and the specimen (i.e., the relative Z position), and measuring the sharpness of the captured images until the image appears in focus. Because measuring the sharpness value of the specimen at a relative Z position will generally not indicate the direction of adjustment (i.e., whether to increase or decrease the distance) required to bring the specimen in focus, a greater number of images and adjustments are generally required to focus an image than if the direction of adjustment were known. This increases the total microscopic scan time of each specimen, which can be detrimental in high throughput scanning applications.

Also, because sharpness measurements can have relatively constant values over relative Z positions near the in-focus position, simply looking for a peak value of a sharpness curve may not accurately identify the in-focus position.

Accordingly, new mechanisms for automatic microscope focus are desirable.

SUMMARY

In accordance with some embodiments, systems, devices and methods for automatic microscope focus are provided. In some embodiments, systems for automatically focusing a microscope are provided, the systems comprising: an objective; a stage for positioning a specimen on a first image forming conjugate plane; a first focusing camera, configured for focusing, positioned on a first side of a second image forming conjugate plane at a first offset distance; a second focusing camera, configured for focusing, positioned on a second side of the second image forming conjugate plane at a second offset distance; wherein the first offset distance and the second offset distance are determined so that sharpness measurements for images of the specimen captured by each of the first focusing camera and the second focusing camera, at a same distance between the objective and the stage, are equal at the second image forming conjugate plane; a primary illumination source; an imaging device positioned on a third image forming conjugate plane; and a hardware processor coupled to the first focusing camera and the second focusing camera that is configured to determine that the specimen is in focus when a sharpness value of the specimen using the first focusing camera is equal to a sharpness value of the specimen using the second focusing camera.

In some embodiments, methods are provided for automatically focusing a microscope having at least an objective, a stage for positioning a specimen on a first image forming conjugate plane, a first focusing camera, configured for focusing, positioned on a first side of a second image forming conjugate plane at a first offset distance, a second focusing camera, configured for focusing, positioned on a second side of the second image forming conjugate plane at a second offset distance, a primary illumination source, an imaging device positioned on a third image forming conjugate plane, the method comprising: setting the first offset distance and the second offset distance so that sharpness measurements for images of the specimen captured by each of the first focusing camera and the second focusing camera, at a same distance between the objective and the stage, are equal at the second image forming conjugate plane; and determining that the specimen is in focus when a sharpness value of the specimen using the first focusing camera is equal to a sharpness value of the specimen using the second focusing camera.

DETAILED DESCRIPTION

In accordance with some embodiments of the disclosed subject matter, mechanisms (which can include systems, methods, devices, apparatuses, etc.) for automatic microscope focus of specimens are provided.

Figure 1A:
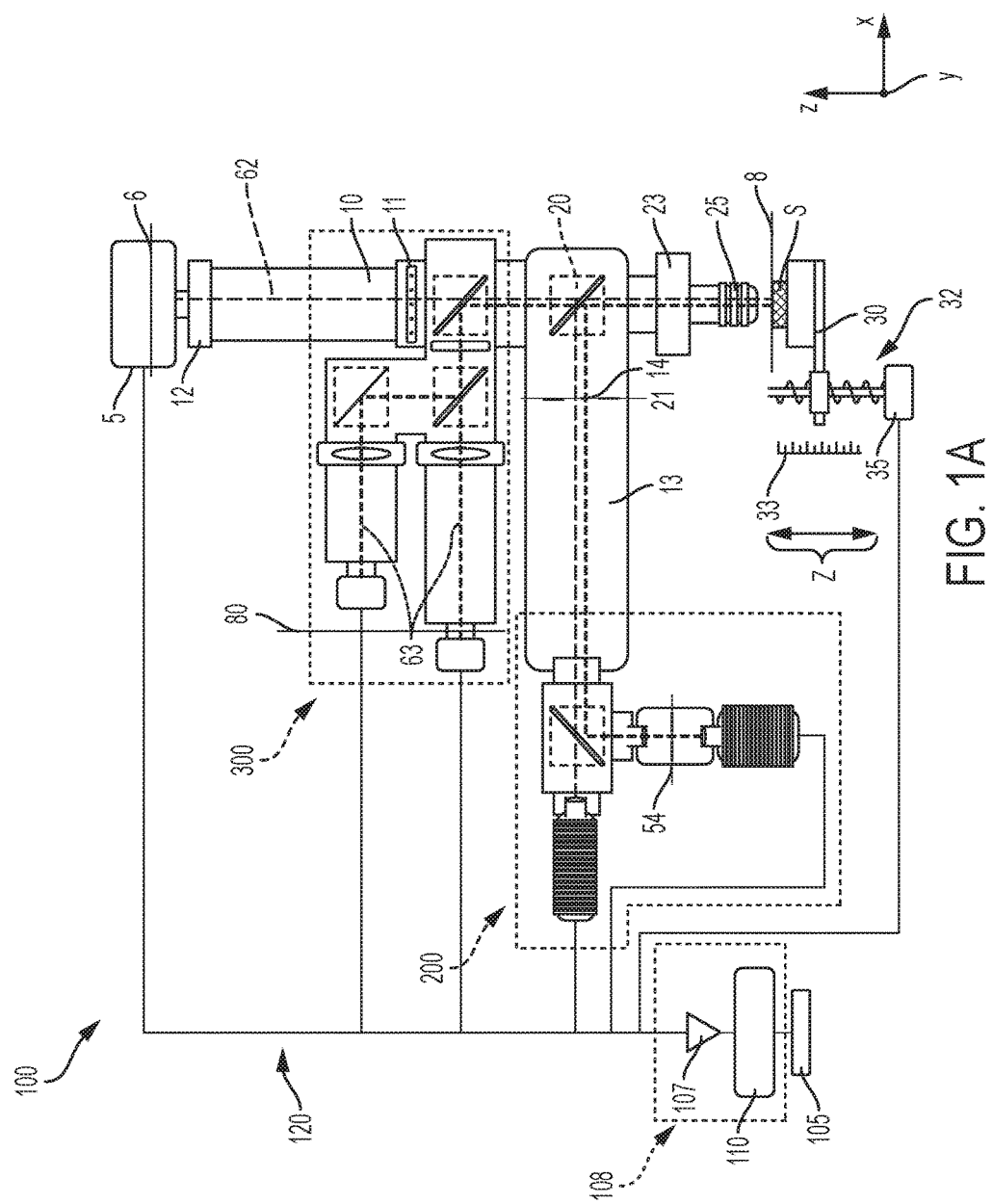
FIG. 1A shows an example of an automatic focus system using two illumination sources in accordance with some embodiments of the disclosed subject matter.
Figure 1B:
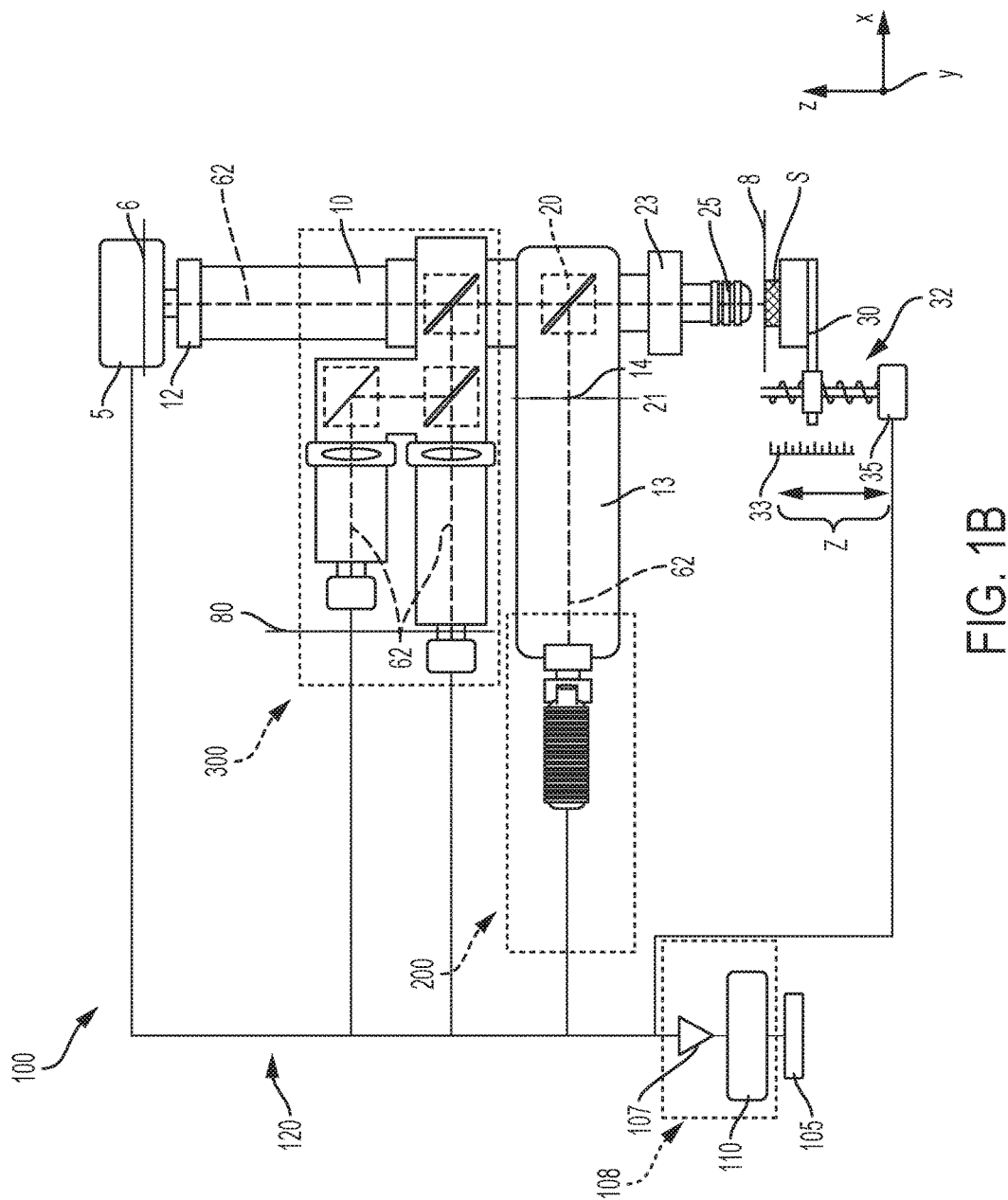
FIG. 1B shows an example of an automatic focus system using one illumination source in accordance with some embodiments of the disclosed subject matter.

FIGS. 1A and 1B illustrate examples of an automatic focus system 100 according to some embodiments of the disclosed subject matter. At a high level, the basic components of automatic focus system 100, according to some embodiments, include an illumination unit 200 for providing light, a focusing unit 300 for finding the in-focus plane of a specimen, an illuminator 13, an imaging device 5, an objective 25, a stage 30, and a control system 108 comprising hardware, software, and/or firmware.

Automatic focus system 100 can be implemented as part of any suitable type of microscope. For example, in some embodiments, system 100 can be implemented as part of an optical microscope that uses transmitted light or reflected light. More particularly, system 100 can be implemented as part of the nSpec® optical microscope available from Nanotronics Imaging, Inc. of Cuyahoga Falls, Ohio Although the following description refers to a reflected light illuminator 13, the mechanisms described herein can be a part of microscopes that do not use a reflected light illuminator.

According to some embodiments, system 100 can include, one or more objectives 25. The objectives can have different magnification powers and/or be configured to operate with brightfield/darkfield microscopy, differential interference contrast (DIC) microscopy and/or any other suitable form of microscopy including fluorescence. The objective and/or microscopy technique used to inspect a specimen can be controlled by software, hardware, and/or firmware in some embodiments.

In some embodiments, a fine focus actuator 23 can be used to drive objective 25 in a Z direction towards and away from stage 30. Fine focus actuator 23 can be designed for high precision and fine focus adjustment of objective 25. Fine focus actuator 23 can be a stepper motor, servo motor, linear actuator, piezo motor, and/or any other suitable mechanism. For example, in some embodiments, a piezo motor can be used and can drive the objective 0 to 50 micrometers (μm), 0 to 100 μm, or 0 to 200 μm, and/or any other suitable range(s) of distances.

In some embodiments, an XY translation stage can be used for stage 30. The XY translation stage can be driven by stepper motor, servo motor, linear motor, piezo motor, and/or any other suitable mechanism. The XY translation stage can be configured to move a specimen in the X axis and/or Y axis directions under the control of any suitable controller, in some embodiments.

In some embodiments, focus mechanism 32, comprising actuator 35, can be used to adjust stage 30 in a Z direction towards and away from objective 25. Actuator 35 can be used to make coarse focus adjustments of, for example, 0 to 5 mm, 0 to 10 mm, 0 to 30 mm, and/or any other suitable range(s) of distances. Actuator 35 can also be used to move stage 30 up and down to allow specimens of different thicknesses to be placed on the stage. Actuator 35 can also be used in some embodiments to provide fine focus of, for example, 0 to 50 μm, 0 to 100 μm, 0 to 200 μm, and/or any other suitable range(s) of distances. In some embodiments, focus mechanism 32 can also include a location device 33. The location device can be configured to determine a position of stage 30 at any suitable point in time. In some embodiments, any suitable position (e.g., the position of the stage when a specimen is in focus) can be stored in any suitable manner and later used to bring the stage back to that position, even upon reset and/or power cycling of autofocus system 100. In some embodiments, the location device can be a linear encoder, a rotary encoder or any other suitable mechanism to track the absolute position of stage 30 with respect to the objective.

In some embodiments, automatic focus system 100, when properly focused and aligned, can use a set of conjugate focal planes, for example an image-forming conjugate set (as shown in FIGS. 1A and 1B), that occur along the optical pathway through the microscope. Each plane within the image-forming conjugate set is conjugate with the others in that set because the planes are simultaneously in focus and can be viewed superimposed upon one another when observing specimens through the microscope. The set of image-forming conjugate planes used in automatic focus system 100 can include a focusing unit image-forming conjugate plane 80 ("focusing conjugate plane 80"), an imaging device image-forming conjugate plane 6 ("imaging conjugate plane 6"), an illumination unit image-forming conjugate plane 54 ("illumination conjugate plane 54"), a field diaphragm (F-stop) image-forming conjugate plane 21 ("field diaphragm conjugate plane 21") and a specimen image-forming conjugate plane 8 ("specimen conjugate plane 8"). All references herein to positioning a first offset focusing camera 70, a second offset focusing camera 72, and/or an imaging camera 5 (when imaging device 5 is a camera), on or offset to an image-forming conjugate plane, refer to positioning the sensors within cameras 5, 70 and/or 72 on or offset to the image-forming conjugate plane. In some embodiments, illumination conjugate plane 54 and/or field diaphragm conjugate plane 21 can be omitted.

In some embodiments, imaging device 5 can be a camera that includes an image sensor that is positioned on image-forming conjugate plane 6 of automatic focus system 100. Imaging device 5 can be used to capture images of a specimen, e.g., once control system 108 determines that the specimen is in focus. The image sensor can be, for example, a CCD, a CMOS image sensor, and/or any other suitable electronic device that converts light into one or more electrical signals. Such electrical signals can be used to form images and/or video of a specimen. In some embodiments, imaging device can be replaced with an ocular or an eyepiece that is used to view a specimen.

In some embodiments, control system 108, comprising controller 110 and controller interface 107, can control any settings of the components of automatic focus system 100 (e.g., actuators 35 and 23, primary illumination source 65, secondary illumination source 40, offset focusing cameras 70 and 72, stage 30, focusing pattern 55, imaging device 5 and objective 25, etc.), as well as communications, operations (e.g., taking images, turning on and off an illumination source, moving stage 30 and objective 25, storing different values associated with a specimen) and calculations (e.g., sharpness calculations) performed by, and between, components of the automatic focus system. Control system 108 can include any suitable hardware (which can execute software in some embodiments), such as, for example, computers, microprocessors, microcontrollers, application specific integrated circuits (ASICs), field-programmable gate arrays (FGPAs) and digital signal processors (DSPs) (any of which can be referred to as a hardware processor), encoders, circuitry to read encoders, memory devices (including one or more EPROMS, one or more EEPROMs, dynamic random access memory ("DRAM"), static random access memory ("SRAM"), and/or flash memory), and/or any other suitable hardware elements. In some embodiments, individual components within automatic focus system 100 can include their own software, firmware, and/or hardware to control the individual components and communicate with other components in automatic focus system 100.

In some embodiments, communication 120 between the control system (e.g., controller 110 and controller interface 107) and the components of automatic focus system 100 can use any suitable communication technologies, such as analog technologies (e.g., relay logic), digital technologies (e.g., RS232, ethernet, or wireless), network technologies (e.g., local area network (LAN), a wide area network (WAN), the Internet) Bluetooth technologies, Near-field communication technologies, Secure RF technologies, and/or any other suitable communication technologies.

In some embodiments, operator inputs can be communicated to the control system using any suitable input device 105 (e.g., a keyboard, mouse or joystick).

Figure 2A:
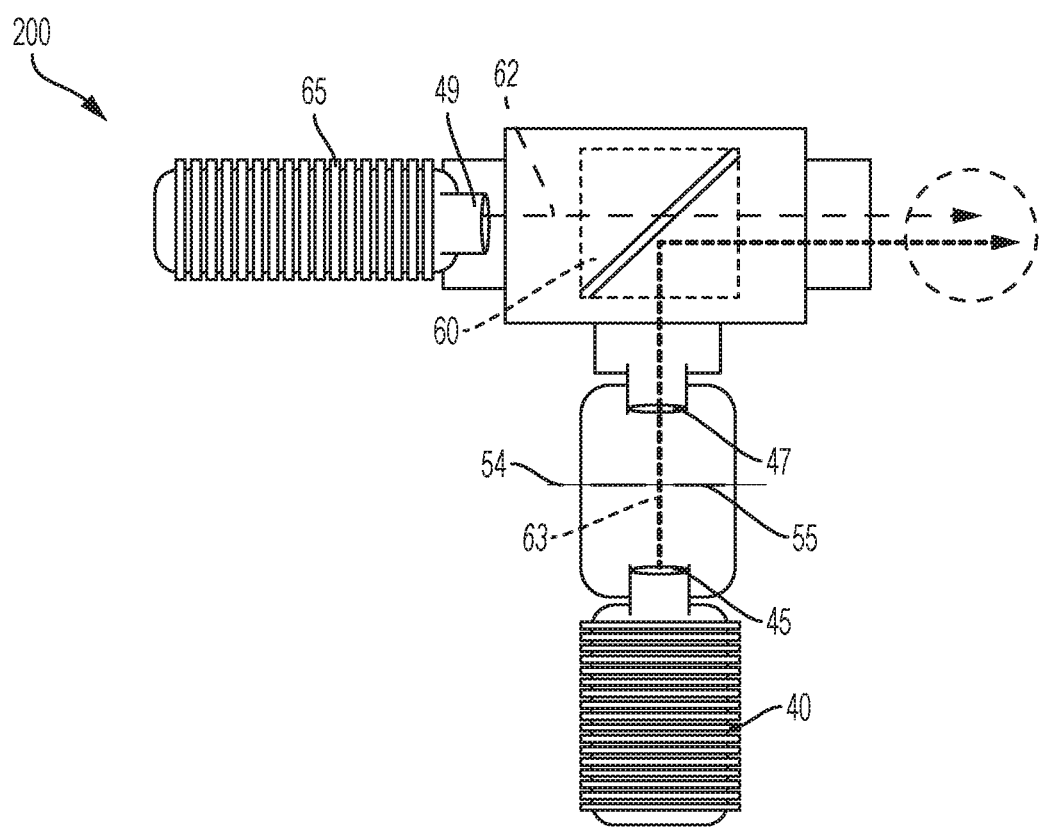
FIG. 2A shows an example of an illumination unit using two illumination sources in accordance with some embodiments of the disclosed subject matter.
Figure 2B:
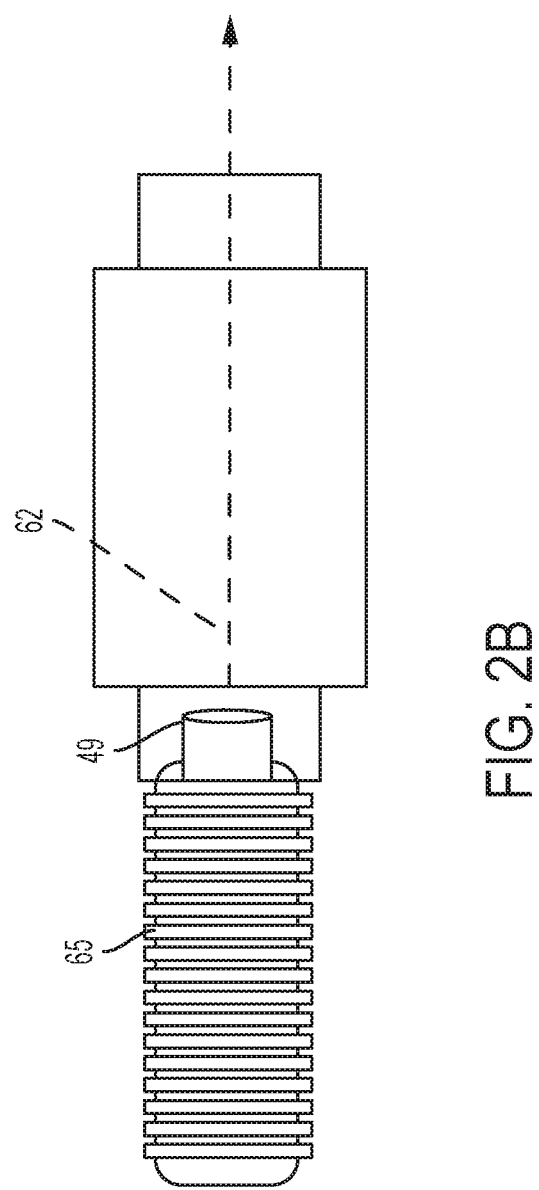
FIG. 2B shows an example of an illumination unit using one illumination source in accordance with some embodiments of the disclosed subject matter.

FIG. 2A shows the general configuration of an embodiment of an illumination unit of the automatic focus system, in accordance with some embodiments of the disclosed subject matter. The illumination unit 200 can include two illumination sources, for example a primary illumination source 65 and a secondary illumination source 40. The illumination sources can provide light beams in ranges of wavelengths that are different from each other. In other embodiments, the illumination unit 200 can include only a primary illumination source 65, as shown, for example, in FIG. 2B.

In some embodiments, for example, primary illumination source 65 provides a light beam having a wavelength in the range of 451 to 750 nanometers (nm), while the secondary illumination source 40 provides a light beam having a wavelength that is higher or lower than the range of wavelengths used for the primary source. For example, the wavelength range of the primary illumination source 65 can be in the range of 550 to 750 nm and the wavelength range of the secondary illumination source can be in the range of 400 to 450 nm. Light of any wavelength range can be used for primary illumination source 65 as long as the value of the range is known and can be separated from other wavelengths using known filtering techniques. Similarly, light of any wavelength range can be used for secondary illumination source 40, as long as the light is not in the same wavelength range as primary illumination source 65.

In some embodiments, as shown in FIG. 1A, primary illumination source 65 is positioned so that its light is transmitted in a horizontal direction towards illuminator 13. Primary illumination source 65 can include a focusing lens 49 (e.g., a double convex lens) for focusing the primary light beam. The secondary illumination source 40 can be positioned at a suitable distance below a focusing pattern 55 located on image-forming conjugate plane 54.

In some embodiments, focusing pattern 55 can be formed from opaque material, with a pattern cut out of the material. The cutout section of the material allows light to pass through to specimen conjugate plane 8, while the opaque material section blocks light from passing through. In other embodiments, focusing pattern 55 can be formed from clear material such as clear glass or clear plastic that has an opaque pattern thereon which causes an image to be projected on the specimen conjugate plane by light passing through the clear glass or plastic. In further embodiments, focusing pattern 55 can be digitally controlled (e.g., a special light modulator).

The diameter of focusing pattern 55 (e.g., 5 mm) can be adjusted so that a projection of focusing pattern 55 is smaller than the field of view (FOV) of offset focusing cameras 70 and 72. Focusing pattern 55 can be any suitable geometric shape for example, a circle, rectangle, triangle, or hexagon and can be projected on any area of the FOV. Focusing pattern 55 can also include a series of discrete openings, so that when light is transmitted through the discrete openings, the lines and spaces are projected across the field of view. In some embodiments, focusing pattern 55 can be customized for a specimen. In some embodiments, the location of primary illumination source 65 and secondary illumination source 40 can be switched.

In some embodiments, automatic focus system 100 can be configured so that light from secondary illumination source 40 is continuously transmitted through focusing pattern 55 in order to continuously project the focusing pattern image on a specimen that can be captured by offset focusing cameras 70 and 72. The continuous projection of the focusing pattern image can facilitate sharpness focus of a specimen, especially for transparent specimens or for specimens that lack any visually recognizable features. Focusing pattern 55 can be used instead of, or in addition to, a field diaphragm, for sharpness focusing. For example, automatic focus system 100, in addition to focusing pattern 55, can also include a field diaphragm (F-stop) 14 that can be located in the illuminator 13. Field diaphragm 14 can also be positioned on an image-forming conjugate plane of automatic focus system 100. In some embodiments, field diaphragm 14 controls the diameter of light emitted by illumination source 65 and 40 and transmitted to objective 25. More specifically, in some embodiments, by reducing the size of the field diaphragm, the diameter of the light passing through is reduced. This creates a dark outline around the image of the specimen received by offset focusing cameras 70 and 72 and can be used to adjust the focus of the specimen (e.g., by moving the specimen and objective closer together or farther apart). At the point of greatest measured sharpness, the specimen is considered to be in-focus and the field diaphragm can be opened to a larger size to allow imaging of the specimen by imaging device 5. Reducing the field diaphragm and returning it to its original size, however, takes time (e.g., 2-5 seconds) and can slow down the scanning process and throughput.

Focusing pattern 55 can be positioned on an any suitable image-forming conjugate plane of automatic focus system 100 (e.g., above secondary illumination source 40 (as shown in FIGS. 1A and 2A), or at field diaphragm 14), as long as an appropriate filter (e.g., filter 11) is used, when necessary, to make sure that focusing pattern 55 is not projected onto imaging device 5. For example, if focusing pattern 55 is positioned on the field diaphragm 14 image forming conjugate plane, in place of field diaphragm 14, then a filter would be necessary. In some embodiments, a band filter can be located on the field diaphragm image forming conjugate plane (in place of field diaphragm 14) and a focusing pattern in the form of a pattern cutout can be created in the band filter. More specifically, a band filter can be selected that transmits light in the same wavelength range of primary illumination source 65 (e.g., greater than 450 nm) and blocks light in the same wavelength range of secondary illumination source 40 (e.g., less than or equal to 450 nm), except in the focusing pattern 55 region. In other words, light in the same wavelength range of secondary illumination 40 source would be blocked except in the region of focusing pattern 55, which would allow the light from secondary illumination 40 to be transmitted through to offset focusing cameras 70 and 72.

In some embodiments, when using a single illumination source, focusing pattern 55 can be digitally controlled (e.g., using a special light modulator) and can be located, for example, on the field diaphragm image forming conjugate plane of automatic system 100. More specifically, in some embodiments, when digitally controlled, focusing pattern 55 can be controlled to be disabled at predetermined intervals, so that imaging device 5 can form electrical signals representing an image and/or video of the specimen without interference from focusing pattern 55 (at full field of view). In some embodiments, imaging device 5 can be configured so that it does not form such electrical signals of a specimen when focusing pattern 55 is enabled.

Note that, in some embodiments, any suitable illumination source(s) can be used with illumination unit 200, such as a 400 nm ultraviolet collimated light-emitting diode (LED) for secondary illumination source 40 and a 5500 K white light collimated LED for primary illumination source 65. In some embodiments, lasers or fluorescent light can be used for primary illumination source 65 and/or secondary illumination source 40.

In some embodiments focusing lens 45 (e.g., a 60 mm focal length bioconvex lens) can be placed at a suitable distance between the secondary illumination source 40 and focusing pattern 55. Further, another focusing lens 47 can be placed at a suitable distance on the other side of focusing pattern 55. In some embodiments, the distance of the lenses 45 and 47 from focusing pattern 55 can be based on the optical characteristics of the microscope to ensure the focusing of the light and positioning of focusing pattern 55 to be in a conjugate image-forming plane.

In some embodiments that use two illumination sources, a dichroic 60 is placed in the optical pathway of both primary illumination source 65 and secondary illumination source 40 before the light travels to illuminator 13. Dichroic, as used herein, can refer to mirrors, beam splitters, filters or beam combiners that transmits light of a known, specified wavelength and combines the transmitted light with a light of another known, specified wavelength. Note that a combination of the aforementioned devices can be used to reflect and transmit the desired illumination sources and wavelengths. In some embodiments, a dichroic having a specific cut-off wavelength is selected in order to reflect the wavelengths of light emitted by secondary illumination source 40 and to allow the wavelengths of light emitted from primary illumination source 65 to pass through. For example, if secondary illumination source 40 emits light in a wavelength range of 400-450 nm and primary illumination source 65 emits light in a wavelength range of 550-750 nm, then a 450 nm cutoff dichroic (i.e., a dichroic that reflects light with a wavelength of 450 nm and below and allows light with a wavelength greater than 450 nm to pass through thereby combining the beams) can be used to reflect light from secondary illumination source 40 and to allow light from primary illumination source 65 to pass through. Dichroic 60 can be designed for a 45° angle of incidence, so that rejected light from secondary illumination source 40 is reflected at an angle of 90° and travels parallel to the light path from primary illumination source 65.

Figure 3A:
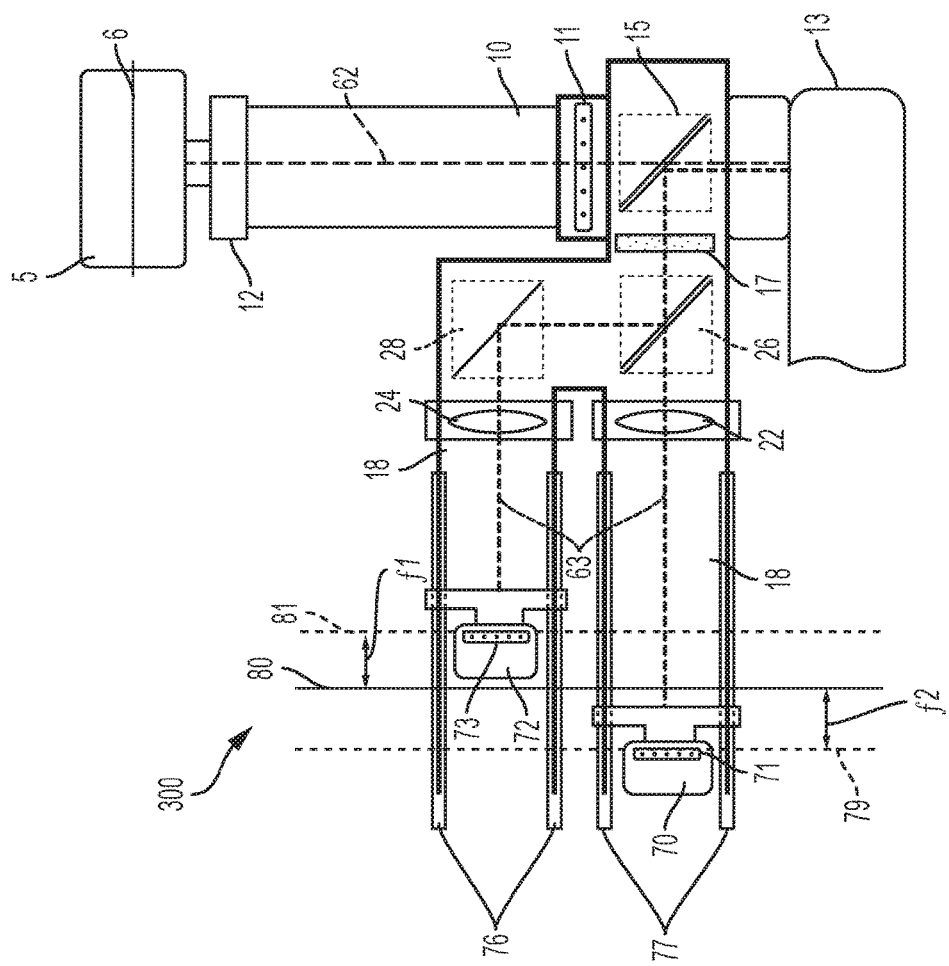
FIG. 3A shows an example of a focusing unit of an automatic focus system using two illumination sources in accordance with some embodiments of the disclosed subject matter.

In some embodiments, primary illumination source 65 can be the light source used for imaging device 5 and secondary illumination source 40 can be the light source used for imaging a specimen on focusing sensors 71 and 73 of offset focusing cameras 70 and 72 (as shown in FIGS. 1A and 3A).

Note that, in some embodiments any suitable dichroic, illuminator, illumination source, focusing lens, sensor and focusing pattern can be used with illuminating unit 200. In some embodiments, any suitable arrangement of these components can be used with illuminating unit 200. In some embodiments, the components of illuminating unit 200 can be mounted to illuminator 13 in any suitable manner, such as by using guide rods in a similar manner to how offset focusing camera 72 is shown as being mounted to focusing housing 18 in FIG. 3 (described below), in order to allow variable geometry.

Figure 3B:
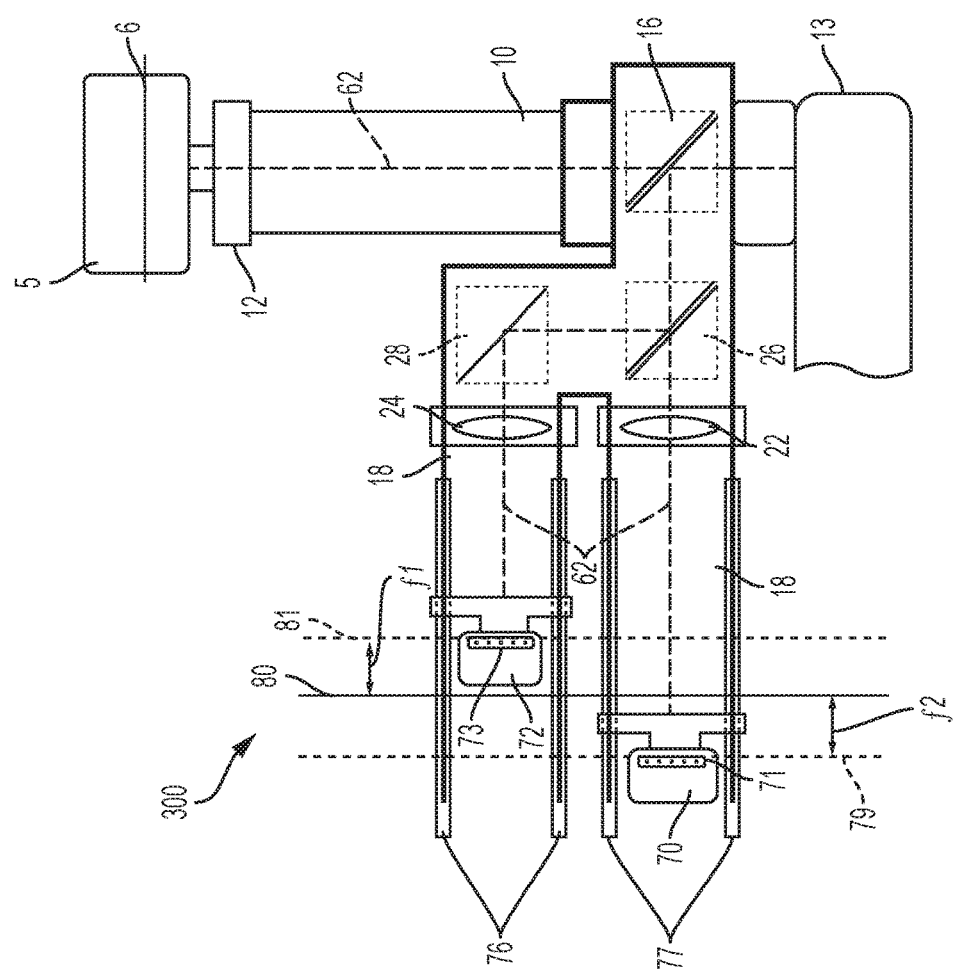
FIG. 3B shows an example of a focusing unit of an automatic focus system using one illumination sources in accordance with some embodiments of the disclosed subject matter.

FIGS. 3A and 3B show an example of a general configuration of an embodiment of a focusing unit of the automatic focus system, in accordance with some embodiments of the disclosed subject matter. The focusing unit 300 can include two cameras: a first offset focusing camera 70 and a second offset focusing camera 72. These cameras can include, for example, a charged coupled device (CCD) image sensor, a CMOS image sensor, another form of image sensor, a video sensor and/or any other suitable sensor that can form electrical signals representative of an image and/or video of a specimen. In some embodiments, such electrical signals can be stored and analyzed by control system 108.

The focusing unit 300 can be mounted in an area between illuminator 13 and imaging microscope tube lens 10. This area can be referred to as infinity space. In some embodiments, the focusing unit 300 can be mounted in other locations using appropriate components to adapt the selected location to the optical characteristics of the system.

First offset focusing camera 70 can include a sensor 71 that is positioned at an offset distance f1 to focusing conjugate plane 80. The offset distance f1 can be either be in the positive direction 81 or in the negative direction 79. A second offset focusing camera 72 can include a sensor 73 that can be positioned at an offset distance f2 to focusing conjugate plane 80. The offset distance f2 can be either be in the positive direction 81 or in the negative direction 79.

As shown in FIGS. 3A and 3B, first offset focusing camera 70 and second offset focusing camera 72 are positioned on different sides of focusing conjugate plane 80. For example, in some embodiments, in which focusing conjugate plane 80 is vertical, first offset focusing camera 70 can be positioned to the left of focusing conjugate plane 80 and second offset focusing camera 72 can be positioned to the right of conjugate plane 80 (as shown in FIGS. 3A and 3B), and vice versa. Further, second offset focusing camera 72 can be located above or below first offset focusing camera 70. In some embodiments (not shown), in which focusing conjugate plane 80 is horizontal, offset focusing camera 70 can be positioned above focusing conjugate plane 80 and offset focusing camera 72 can be positioned below focusing conjugate plane 80, and vice versa. Further, second offset focusing camera 72 can be located to the right or to the left of offset focusing camera 70. As discussed in connection with FIGS. 5-7, offset focusing cameras 70 and 72 can be positioned so that sharpness values for images and/or video of a specimen captured by offset focusing cameras 70 and 72 will be the same at focusing conjugate plane 80.

First offset focusing camera 70 can be movable along guide rods 77 or any other suitable structure in order to adjust an offset distance of first offset focusing camera 70. Second offset focusing camera 72 can be movable along guide rods 76 or any other suitable structure in order to adjust an offset distance of second offset focusing camera 72.

Focusing unit 300 can also include two focusing lenses 24 and 22. Focusing lens 22 can be placed in the same horizontal optical pathway as first offset focusing camera 70 and focusing lens 24 can be placed in the same horizontal optical pathway as second offset focusing camera 72. In some embodiments, focusing lenses 22 and 24 achieve the same focal distance as microscope tube lens 10, to ensure that sensors 71 and 73 are each in focus when they are positioned on focusing conjugate plane 80. Microscope tube lens 10 can include a lens (not shown) for focusing an image of a specimen on imaging conjugate plane 6, so that the specimen is in focus when an image sensor or ocular is positioned on image conjugate plane 6 of automatic focus system 100.

Note that in some embodiments, lenses 22 and 24 can be double convex lenses or any other suitable type lenses. In some embodiments, the focal length of the lenses can be based on the optical characteristics of the microscope.

As also shown in FIG. 3A, in some embodiments that include two illumination sources (as represented by the pair of longer dashed lines 62 and shorter dashed lines 63), focusing unit 300 can also include a cutoff dichroic 15 that is positioned above illuminator 13 in the optical pathway of the light reflected off a specimen. The dichroic 15 can be positioned so that the light reflected off the specimen that is below the cutoff of the dichroic is reflected at an angle of 90° towards first offset focusing camera 70. A dichroic having a specific cut-off wavelength can be used in order to reflect the wavelengths of light emitted by secondary illumination source 40 (the "focusing beam"). For example, if the focusing beam is in the range of 400 to 450 nm, then a 450 nm cut-off filter can be used with focusing unit 300 in order to reflect the focusing beam towards first offset focusing camera 70. In some embodiments, dichroic 15 is used only in embodiments that include secondary illumination source 40.

In embodiments including two illumination sources, a cut-off filter 17 can be positioned between dichroic 15 and beam splitter 26 to filter out any light coming from primary illumination source 65 (the "imaging beam"). For example, if imaging beam has a wavelength in the range of 450 nm and above, then a 450 nm cutoff filter can be used to filter out the imaging beam and prevent the imaging beam from transmitting light to focusing cameras 70 and 72. In other embodiments, two cut-off filters can be used and each filter can be placed, for example, in front of or behind lenses 22 and 24.

In embodiments that include only a single illumination source, as shown in FIG. 3B (as represented by lines 62) beam splitter 16, can be positioned above illuminator 13 in the optical pathway of the light reflected off a specimen. Beam splitter 16 can be, for example, a 50/50 beam splitter designed to send 50% of the light from primary illumination source 65 to offset focusing cameras 70 and 72, and 50% of the light from primary illumination source 65 to imaging device 5.

In some embodiments, as shown in FIGS. 3A and 3B, focusing unit 300 can include a beam splitter 26 that can be positioned between dichroic 15/beam splitter 16 and first offset focusing camera 70. Beam splitter 26 can be, for example, a 50/50 beam splitter designed to send 50% of the focusing light beam to first offset focusing camera 70 and 50% of the focusing light beam to second offset focusing camera 72. A mirror 28 can be placed at a distance directly above beam splitter 26 and can be designed to direct the beam of light from beam splitter 26 to second offset focusing camera 72.

Note that, in some embodiments any suitable dichroic, focusing camera, focusing lens, mirror, image sensor, beam splitter and cut-off filter can be used with focusing unit 300. In some embodiments, any suitable arrangement of these components can be used with focusing unit 300. The components of focusing unit 300 can be mounted to guide rods or any other suitable structure for connecting the components.

FIGS. 1A and 1B shows example optical pathways, represented by a single or pair of dashed lines 62 and 63, for automatic focus system 100, in accordance with some embodiments of the disclosed subject matter. As shown in FIG. 1A automatic focus system 100 can be configured so that the light emitted from secondary illumination source 40 (the "focusing beam (FB)," as represented by the shorter dashed lines 63) is projected onto specimen S and then reflected to offset focusing cameras 70 and 72. Autofocus system 100 can also be configured so that light emitted from primary illumination source 65 (the "imaging beam (IB)," as represented by the longer dashed lines 62) is projected onto specimen S and then reflected to imaging device 5.

More specifically, in embodiments that use two illumination sources, focusing beam 62 can travel from illumination source 40 through focusing pattern 55 to dichroic 60. Dichroic 60 can reflect focusing beam 62 towards illuminator 13. The imaging beam can travel from primary illumination source 65, pass through dichroic 60 to combine with the focusing beam.

The combined beam (if using two illumination sources) can then travel through illuminator 13 to prism 20. Prism 20 can reflect the light coming from the illumination sources at 90° downwards through a nosepiece and objective 25 to a specimen S. Specimen S can reflect the combined or single beam upwards through objective 25, which is then transmitted through prism 20 towards dichroic 15. Dichroic 15 (if using two illumination sources) can separate the transmitted beam back into imaging beam 62 and focusing beam 63 by, for example, reflecting the wavelengths of the light from secondary illumination source 40 towards offset focusing cameras 70 and 72 and by allowing the wavelengths of the light from primary illumination source 65 to pass through towards camera 5.

In embodiments that include two illumination sources (as shown in FIGS. 1A, 2A and 3A), focusing beam 63 that is reflected by dichroic 15 can pass through cutoff filter 17 to remove any light above the cutoff wavelength. Focusing beam 63 can then travel to beam splitter 26. Beam splitter 26 can send, for example, 50% of focusing beam 63 towards first offset focusing camera 70 by directing the light through focusing lens 22 located in focusing housing 18. From there focusing beam 63, can travel to a light sensor 71 in first offset focusing camera 70. The other 50% of focusing beam 63 can be directed by beam splitter 26 upwards towards mirror 28. Mirror 28 can reflect focusing beam 63 towards focusing lens 24 locating in focusing housing 19. From there focusing beam 63 can be directed to sensor 73 in second offset focusing camera 72.

In some embodiments that include two illumination sources (as shown in FIGS. 1A, 2A and 3A), imaging beam 62 that passes through dichroic 15 can pass through an optical filter 11 (e.g., a filter that transmits only the wavelengths from the imaging beam), up through microscope tube lens 10, and to imaging device 5.

In embodiments that include a single illumination source, as shown in FIG. 1B, autofocus system 100 can be configured so that light emitted from primary illumination source 65 is projected onto specimen S and then reflected to offset focusing camera 70 and 72 and imaging device 5. More specifically, beam splitter 16, can be positioned above illuminator 13 in the optical pathway of the light reflected off the specimen S. Beam splitter can direct, for example, 50% of the light reflected off of specimen S to offset focusing cameras 70 and 72, and 50% to imaging device 5.

In some embodiments, the specimen can be brought into focus using imaging device 5 by moving the objective and the stage closer together or farther apart along a Z axis (as shown in FIGS. 1A and 1B) to different relative Z positions. In some embodiments, focus can be adjusted using a coarse focus adjustment, which spans a wide range of Z-positions (such as 500 μm to 2500 μm, or any other suitable range), and/or using a fine focus adjustment, which spans a more-narrow range of Z-positions (such as 1400 μm to 1600 μm, or any other suitable range). The coarse focus adjustment can be made by actuator 35, in some embodiments. The fine focus adjustment can be made by fine focus actuator 23, in some embodiments.

Figure 4:
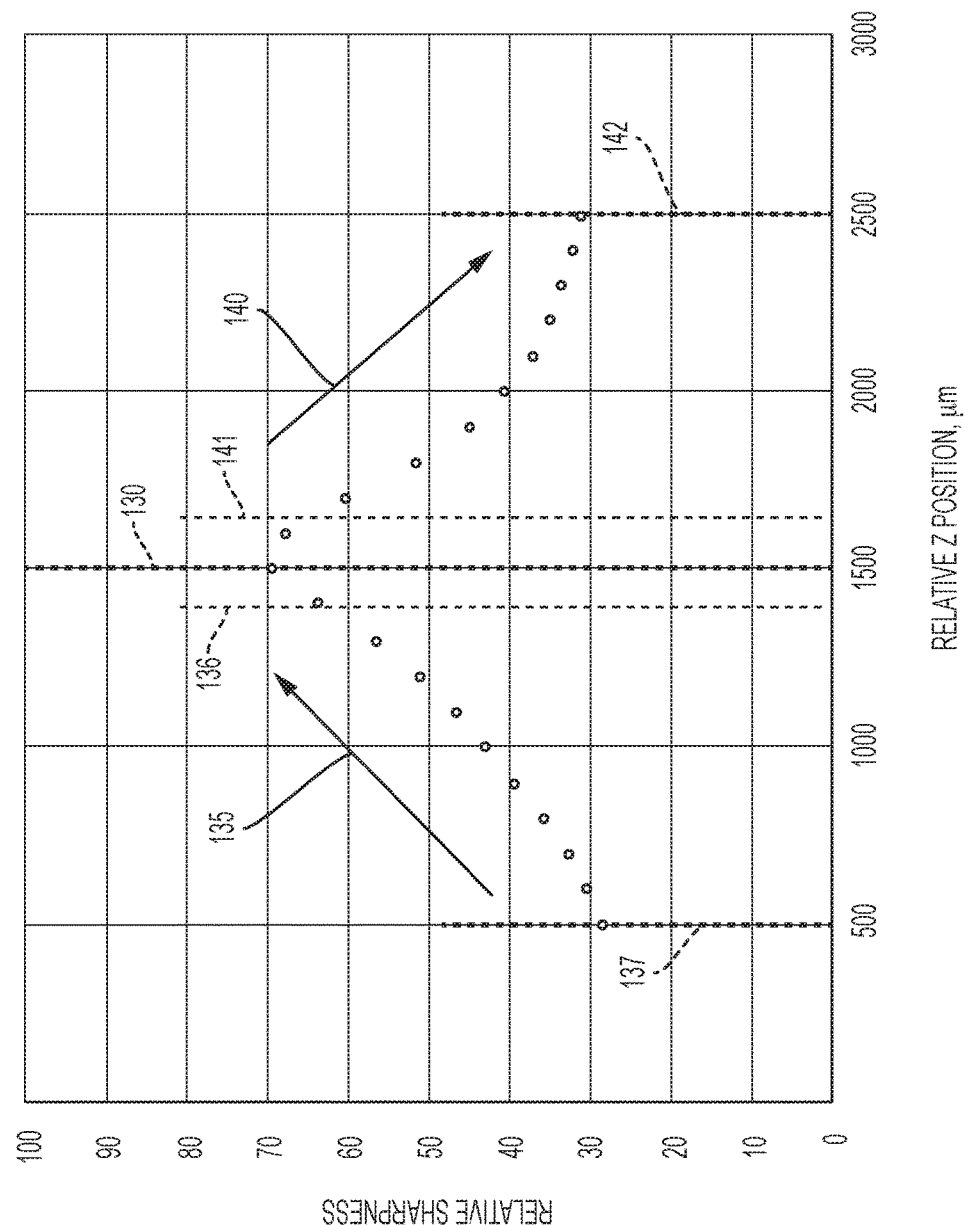
FIG. 4 shows an example of a sharpness curve for an imaging device in accordance with some embodiments of the disclosed subject matter.

In some embodiments, a relative sharpness value of an image formed from light impacting an image sensor can be used as an indicator of the quality of focus of the specimen. In some embodiments, the higher the relative sharpness value, the more in focus the image is. In some embodiments, as shown in FIG. 4, a plot of relative sharpness values over different relative Z positions can have a distinct peak (this can be a single point or several points) at the point of focus and decrease on either side of the focal plane. Relative sharpness values can be formed from any suitable metrics, such as image contrast, resolution, entropy, variance, and/or spatial frequency content, among other measurements, to measure the quality of focus of images captured by a microscope. One example equation that can be used by automatic focus system 100 to calculate a relative sharpness value is a measure of image variance V, normalized by the mean μ to account for intensity fluctuations:

$$V = \frac{1}{\mu} \sum_{i=1}^{N} \sum_{j=1}^{M} [s(i, j) - \mu]^2$$

where mean μ is the mean of the grayscale pixels values of all pixels, s(i,j) is the grayscale pixel value at coordinates (i,j) and N and M represent the number of pixels in the i and j directions respectively. Other example methods for calculating a quality of focus value that can be used by automatic focus system 100 are described by Sivash Yazdanfar et al., "Simple and Robust Image-Based Autofocusing for Digital Microscopy," Optics Express Vol. 16, No. 12, 8670 (2008), which is hereby incorporated by reference herein in its entirety. The above disclosed methods are just examples and are not intended to be limiting.

FIG. 4 shows a graph comprising an X axis that represents the relative position of the top of stage 30 in a Z direction with respect to objective 25 (the "relative Z position") and a Y axis representing a relative sharpness value. The relative Z position can be changed by adjusting a stage 30 towards or away from objective 25 and/or by adjusting objective 25 towards or away from stage 30. The sharpness curve in FIG. 4 shows, at each relative Z position, a relative sharpness value of an image captured/viewed by imaging device 5. As shown in FIG. 4, the sharpness curve can have a maximum measured sharpness (e.g., a relative sharpness value of 70 in FIG. 4) at a given relative Z position (e.g., Z position 130) (that can be referred to as the in-focus position) and may decrease symmetrically on each side of the in-focus position (e.g., Z position 130). In some instances, the slope of the curve in FIG. 4 at the in-focus position can be zero or close to zero. It should be understood that the term "in-focus" as used herein is intended to denote when the relative positioning of the objective and the stage are such that a sharpness measurement is at a point at or near the top of a sharpness curve. The term "in-focus" is not intended to be limited to perfect or optimal focus. In-focus can be defined mathematically, by an operator and/or other suitable methods. The data shown in FIG. 4 can be compiled through a continuous measure (e.g., a sharpness curve) or discrete points that can be collected by varying the relative Z position.

Figure 5:
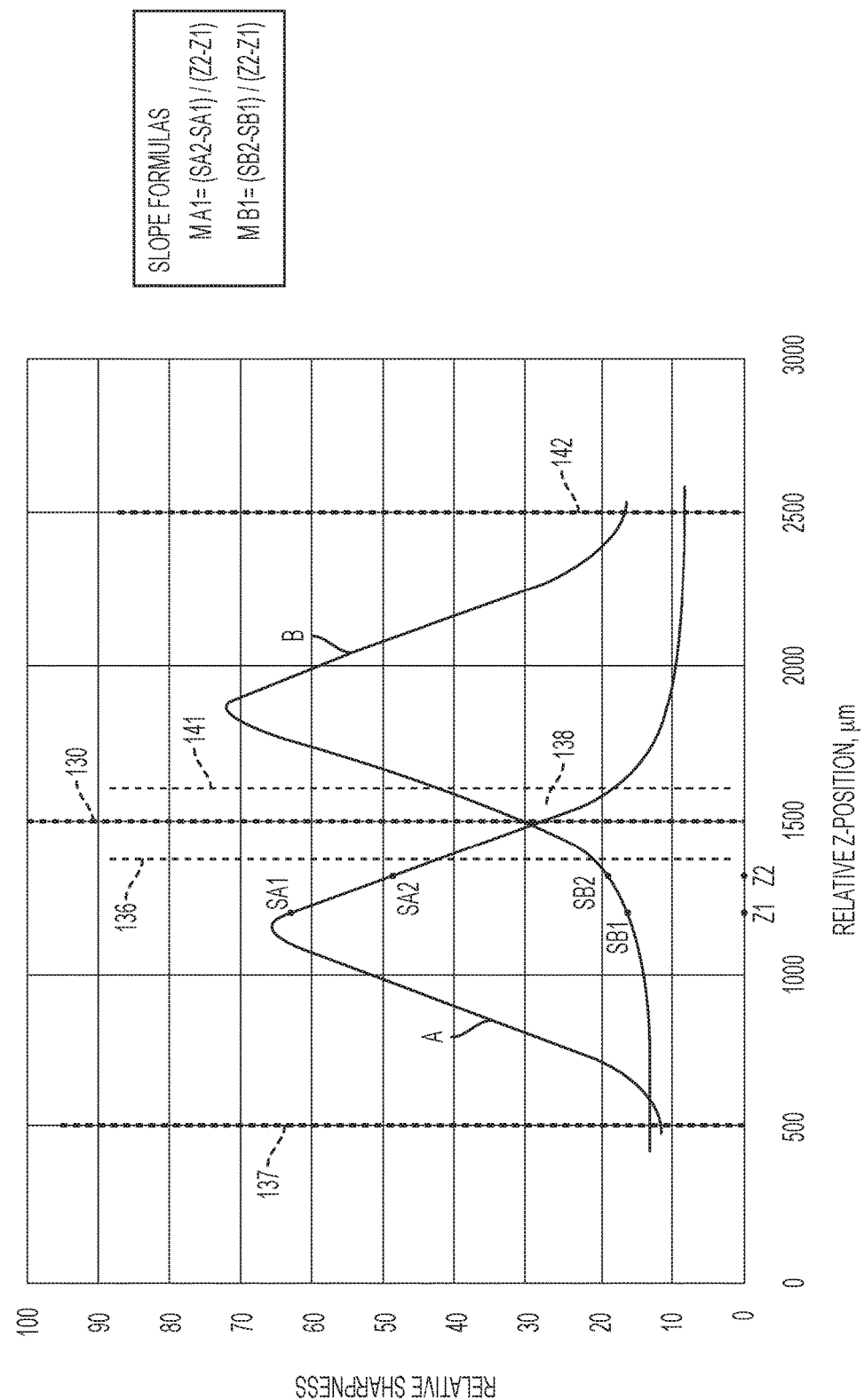
FIG. 5 shows an example of sharpness curves for two offset focusing cameras in accordance with some embodiments of the disclosed subject matter.

The range of coarse Z movement is represented by lines 137 (e.g., at 500 um) and 142 (e.g., at 2500 μm) in FIG. 4 and FIG. 5. The range of fine focus Z movement is represented by lines 136 (e.g., at 1400 μm) and 141 (e.g., at 1600 μm) in these figures. Note, that the range of Z movement refers to a practical range of movement to achieve different Z positions between objective 25 and stage 30. The range of Z movement also refers to the range of Z movement where a sharpness calculation can be used to focus a specimen. Arrow 135 shows the sharpness score increasing to a maximum point at Z position 130 (indicating that the image is considered to be in focus as described above) as stage 30 and objective 25 move farther apart and arrow 140 shows the sharpness score decrease from maximum point at Z position 130 as stage 30 and objective 25 continue to move farther apart.

It should be apparent that the relative sharpness values and the Z positions illustrated in FIGS. 4 and 5 are just examples and that other value combinations may be measured in any given application.

As mentioned above, in some instances, the slope of the curve in FIG. 4 at the in-focus position can be zero or close to zero. This can make finding a single best focus position difficult.

As described in detail below, cameras 70 and 71 can be used to help find an in-focus position of a specimen even when the slope of the curve in FIG. 4 at the in-focus position is zero or close to zero.

FIG. 5 shows sharpness curves A and B for images of a specimen taken by offset focusing cameras 70 and 72 respectively. Similar to FIG. 4, the X axis of the graph represents relative Z positions, the Y axis represents relative sharpness values and line 130 represents focusing conjugate plane 80 and indicates the Z position where the maximum measured sharpness value for a specimen, using imaging device 5, may be found. Sharpness curve A shows, at each relative Z position, the relative sharpness value of an image captured by first offset focusing camera 70. Sharpness curve B shows, at each relative Z position, the relative sharpness value of an image captured by second offset focusing camera 72. FIG. 5 shows that the negative slope of curve A and the positive slope of curve B intersect at focusing conjugate plane 80, at 138. At 138, the sharpness values of images captured by each of offset focusing cameras 70 and 72 of a specimen at the same Z position (i.e., 1500 μm) are the same. In some embodiment, the data shown in FIG. 5 can be compiled through a continuous measure (e.g., a sharpness curve) or discrete points that can be collected by varying the relative Z position. In some embodiments, the curves in FIG. 5 are not known.

Using the properties of curves A and B for cameras 70 and 72 illustrated in FIG. 5, system 100 can be configured to sample relative sharpness values at two relative Z positions for each of cameras 70 and 72 and use the resulting sharpness values and relative Z positions to determine the direction of needed relative movement of the stage and the objective (i.e., whether to increase or decrease the relative Z position) in order to bring the specimen into focus. Moreover, in some embodiments, system 100 can additionally be configured to use the resulting sharpness values and relative Z positions to determine the amount of needed relative movement of the stage and the objective (i.e., the amount of change in the relative Z position) in order to bring the specimen into focus.

More particularly for example, in some embodiments, by determining the slope of a line between two relative Z positions along curve A and by determining the slope of a line between the same two relative Z positions along curve B, one can determine whether the current relative Z position is: to the left of the peak of curve A, between the peak of curve A and the focal point, between the focal point and the peak of curve B, or to the right of the peak of curve B. Upon knowing this information, the direction of required movement is known. That is, if the current relative Z position is to the left of the peak of curve A, or between the peak of curve A and the focal point, then the relative position needs to increase. If the current relative Z position is between the focal point and the peak of curve B, or to the right of the peak of curve B, then the relative position needs to decrease.

Figure 6:
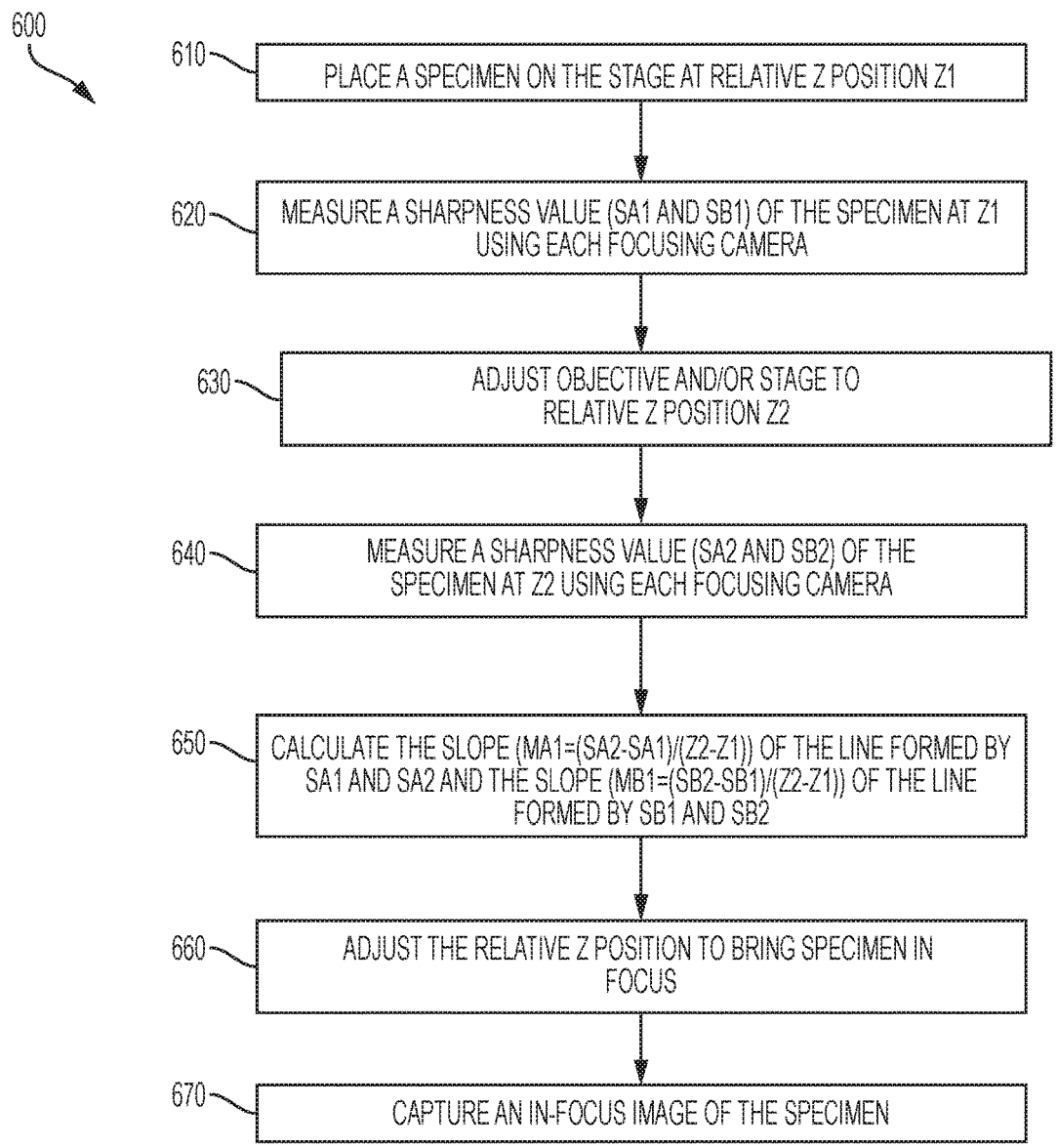
FIG. 6 shows an example of a flow chart of a process for performing automatic focus using an automatic focus system, such as the system illustrated in FIGS. 1A and 1B, in accordance with some embodiments of the disclosed subject matter.

FIG. 6, with further reference to FIGS. 1-5, shows an example process 600 for bringing a specimen in-focus in automatic focusing system 100, in accordance with some embodiments of the disclosed subject matter.

At 610, a specimen is placed on stage 30. Stage 30 and/or objective 25 can be moved until a top surface of stage 30 is positioned at a position Z1 within the operating range as defined by Z positions 137 and 142.

At 620, a sharpness value of the specimen at relative Z position Z1 can be measured using each of offset focusing cameras 70 and 72. The sharpness value SA1 for an image of specimen S, captured by focusing camera 70, can be recorded, along with the Z1 position. The sharpness value SB1 for an image of specimen S, captured by focusing camera 72 can be recorded, along with the Z1 position.

At 630, stage 30 and/or objective 25 can be moved until specimen S is at a different relative Z position Z2 within Z positions 137 and 142. In some embodiments, position Z2 can be selected so that the distance between Z1 and Z2 is twice the distance of the depth of focus (DOF) of objective 25 or another multiple that is less than 2 (e.g., 1.5 times DOF, 1 times DOF or 0.5 times DOF). The disclosed method for selecting position Z2 is just an example and not intended to be limiting.

Next, at 640, similarly to 620, a sharpness value of the specimen at relative Z position Z2 can be measured using each of offset focusing cameras 70 and 72. The sharpness value SA2 for an image of specimen S, captured by focusing camera 70, can be recorded, along with the Z2 position. The sharpness value SB2 for an image of specimen S, captured by focusing camera 72 can be recorded, along with the Z2 position.

At 650, the slope MA1 of a line formed between (Z1,SA1) and (Z2,SA2) can be calculated and recorded. For example, MA1 can be equal to (SA2−SA1)/(Z2−Z1). Similarly, the slope MB1 of the line formed between (Z1,SB1) and (Z2,SB2) can be calculated and recorded. For example, MB1 can be equal to (SB2−SB1)/(Z2−Z1).

At 660, the relative Z position can be adjusted to bring specimen S into focus. In some embodiments, the relative Z position can be adjusted to bring specimen S into focus in any suitable manner. For example, in some embodiments, the relative Z position can be adjusted to bring specimen S into focus by performing the Z adjustments listed for different combinations of values of MA1, MB1, SA2, and SB2 as detailed in the following table.

| If Value of MA1 and MB1 is: | Then Make Z Adjustment |
| --- | --- |
| MA1 is positive; and MB1 is positive or 0 | Increase the relative Z position until the sharpness values for images of the specimen captured by offset focusing cameras 70 and 72 are the same (or are within any suitable tolerance of each other) (e.g., as indicated by point of intersection 138 in FIG. 5) and the direction of slopes MA2 and MB2 (as described below) at the point of intersection are opposite each other. |
| MA1 is negative or 0; and MB1 is negative | Decrease the relative Z position until the sharpness values for images of the specimen captured by offset focusing cameras 70 and 72 are the same (or are within any suitable tolerance of each other) (e.g., as indicated by point of intersection 138 in FIG. 5) and the direction of slopes MA2 and MB2 (as described below) at the point of intersection are opposite each other. |
| MA1 is negative or 0; and MB1 is positive or 0; and The value of SA2 is greater than SB2 | Increase the relative Z position until the sharpness values for images of the specimen captured by offset focusing cameras 70 and 72 are the same (or are within any suitable tolerance of each other) (e.g., as indicated by point of intersection 138 in FIG. 5) and the direction of slopes MA2 and MB2 (as described below) at the point of intersection are opposite each other. |
| MA1 is negative or 0; and MB1 is positive or 0; and The value of SA2 is less than SB2 | Decrease the relative Z position until the sharpness values for images of the specimen captured by offset focusing cameras 70 and 72 are the same (or are within any suitable tolerance of each other) (e.g., as indicated by point of intersection 138 in FIG. 5) and the direction of slopes MA2 and MB2 (as described below) at the point of intersection are opposite each other. |

The point of intersection can occur when images captured by focusing camera 70 and 72 have the same sharpness value (or are within any suitable tolerance of each other) at the same relative Z position (as indicated by 138 in FIG. 5).

The disclosed table is just an example method for focusing a specimen using offset focusing cameras 70 and 72 and is not intended to be limiting. Other methods for focusing a specimen using offset focusing cameras 70 and 72 can be used.

In performing what is described in the table above, when adjusting (i.e., increasing or decreasing) the relative Z position until the sharpness values for images of the specimen captured by offset focusing cameras 70 and 72 are the same (or are within any suitable tolerance of each other), system 100 can perform any suitable actions. For example, in some embodiments, system 100 can adjust the relative Z position in the indicated direction by a given amount, repeat 620, determine if the sharpness values for images of the specimen captured by offset focusing cameras 70 and 72 are the same (or are within any suitable tolerance of each other), and, if the values are not the same (or within the tolerance), then repeat 630, 640, and 650 until the sharpness values for images of the specimen captured by offset focusing cameras 70 and 72 are the same (or are within any suitable tolerance of each other) (e.g., as indicated by point of intersection 138 in FIG. 5) and the direction of slopes MA2 and MB2 (as described below) at the point of intersection are opposite each other.

Any suitable given amount(s) of movement can be used at 650, and the given amount(s) can be determined in any suitable manner. For example, in some embodiments, the given amount can always be a fixed amount. This fixed amount can be determined based on the configurations of system 100 and can be user specified. As another example, in some embodiments, the given amount can vary based on the slopes determined at 640. More particularly, the given amount can be larger when the slopes indicate that the relative Z position is to the left of the peak of curve A in FIG. 5 or to the right of the peak of curve B in FIG. 5, and the given amount can be smaller when the slopes indicate that the relative Z position is between the peak of curve A in FIG. 5 and the peak of curve B in FIG. 5. As still another example, the given amount can be based on the slopes determined at 640 and be a function of the values of SA1 and SB1 determined at 620. More particularly, when the slopes indicate that the relative Z position is to the left of the peak of curve A in FIG. 5 or to the right of the peak of curve B in FIG. 5, the given amount can be inversely proportional to the difference between SA1 and SB1 (i.e., when the difference between SA1 and SB1 is small, the given amount will be large, and when the difference between SA1 and SB1 is large, the given amount will be small), and when the slopes indicate that the relative Z position is between the peak of curve A in FIG. 5 and the peak of curve B in FIG. 5, the given amount can be proportional to the difference between SA1 and SB1 (i.e., when the difference between SA1 and SB1 is small, the given amount will be small, and when the difference between SA1 and SB1 is large, the given amount will be large) (in this example, the given amount can be prevented from dropping below a minimum value so that intersection 138 can be found quickly).

As indicated in the table above, when adjusting the relative Z position to bring specimen S into focus, process 600 can determine whether the direction of slopes MA2 and MB2 are opposite each other. To determine the direction of the slopes MA2 and MB2 at the point of intersection, stage 30 and/or objective 25 can first be moved from the point of intersection until specimen S is at a different position Z3 within Z positions 137 and 142. In some embodiments, position Z3 can be selected so that its distance from the point of intersection is twice the depth of focus (DOF) of objective 25 or another multiple that is less than 2 (e.g., 1.5 times DOF, 1 times DOF or 0.5 times DOF). The disclosed method for selecting position Z3 is just an example and not intended to be limiting.

Next, sharpness values SA3 and SB3 and Z3 position can be recorded for images of the specimen captured by offset focusing cameras 70 and 72.

Then, the slope MA2 of a line formed between the point of intersection and (Z3,SA3), and the slope MB2 of a line formed between the point of intersection and (Z3,SB3), can be calculated.

If the direction of the slopes MA2 and MB2 are opposite to each other, then the point of intersection is at the image-forming conjugate plane. Otherwise, the stage and/or objective can be continued to be adjusted according to the instructions in the table above.

In some embodiments, the sharpness value at the point of intersection can be compared to a recorded sharpness setpoint for automatic focus system 100, a particular specimen, specimen class and/or any other suitable classification group. If the sharpness value at the point of intersection is the same or within an acceptable variance of the recorded sharpness value, then the point of intersection occurs when the point of intersection is at the image-forming conjugate plane. Otherwise, the stage and/or objective can be continued to be adjusted according to the instructions in the table above.

In some embodiments, once the relative Z position where the specimen is in-focus is determined, the absolute position of: stage 30; objective 25; the top of the specimen on stage 30; and/or the distance between the top of stage 30 and objective 25, can be stored by control system 108 as a position setpoint. The position setpoint can be associated with a particular specimen, a particular specimen class and/or any other suitable classification group for the specimen.

Because the slopes, along with certain points, on sharpness curves A and B indicate whether the distance between the stage and objective must be decreased or increased to bring the specimen in focus, fewer images of the specimen can be taken to bring a specimen into focus.

At 670, in some embodiments, once the specimen is determined to be in-focus, an in-focus image can be captured by imaging device 5.

In some embodiments, once the specimen is determined to be in-focus using the method described in 610-660, imaging device 5 can be used to fine tune the focus of the specimen. For example, using imaging device 5, sharpness values of the specimen can be calculated for at least two relative Z positions of the stage and objective to determine whether an estimated maximum sharpness has been achieved or the relative Z-position needs to be adjusted to achieve an estimated maximum sharpness (i.e., the point on the sharpness curve where the slope is 0 or close to 0).

In some embodiments, control system 108 can also determine whether there is a position setpoint associated with the specimen, specimen class and/or any other suitable classification group for the specimen placed on stage 30, and can position autofocus system 100 at that position setpoint at 610. Knowing an approximate target relative Z position, reduces the relative Z distance that is needed to focus the specimen and allows the offset focusing cameras to be positioned closer to focusing conjugate plane 80. As discussed above, the slope of the sharpness curves become steeper as offset focusing cameras 70 and 72 move closer to focusing conjugate plane 80. A steeper slope, represents greater resolution or a larger change in sharpness versus a smaller change in Z height. A steeper slope can allow for finer focal adjustment and control.

The division of when the particular portions of process 600 are performed can vary, and no division or a different division is within the scope of the subject matter disclosed herein. Note that, in some embodiments, blocks of process 600 can be performed at any suitable times. It should be understood that at least some of the portions of process 600 described herein can be performed in any order or sequence not limited to the order and sequence shown in and described in FIG. 6 in some embodiments. Also, some of the portions of process 600 described herein can be or performed substantially simultaneously where appropriate or in parallel in some embodiments. Additionally or alternatively, some portions of process 600 can be omitted in some embodiments.

Process 600 can be implemented in any suitable hardware and/or software. For example, in some embodiments, process 600 can be implemented in control system 108 shown in FIG. 1.

The location of focusing conjugate plane 80 can be determined in any suitable manner in some embodiments. For example, in some embodiments, focusing conjugate plane 80 can be determined mathematically based on characteristics of automatic focus system 100.

Figure 7:
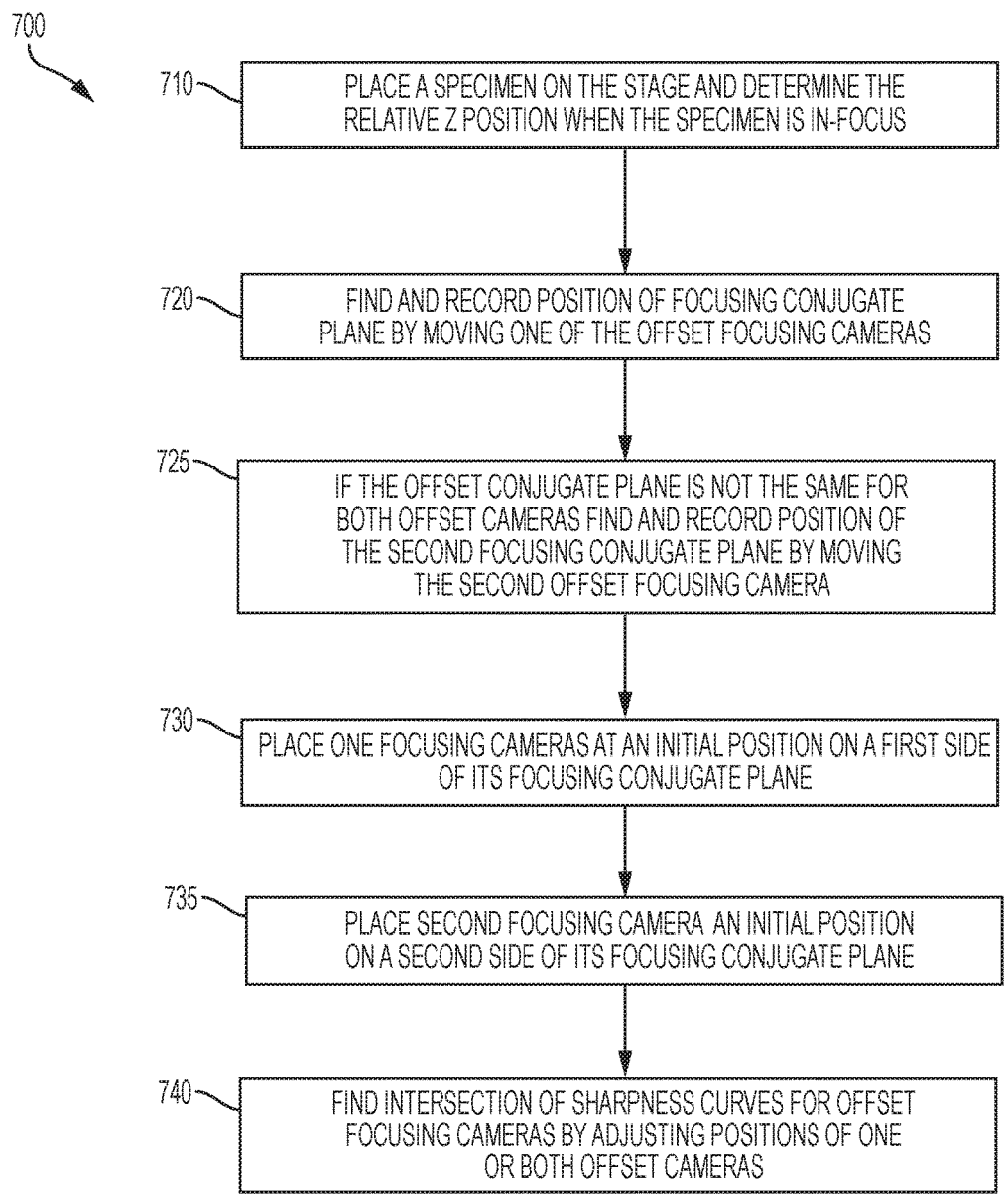
FIG. 7 shows an example of a flow chart of a process for finding an image-forming conjugate plane and calibrating two offset focusing cameras, using an automatic focus system, such as the system illustrated in FIGS. 1A and 1B, in accordance with some embodiments of the disclosed subject matter.

As another example, in some embodiments, focusing conjugate plane 80 can be determined using a calibration process. FIG. 7, with further reference to FIGS. 1-6, shows an example of a calibration process 700 for finding focusing conjugate plane 80 and calibrating offset distances f1 and f2 for offset focusing cameras 70 and 72 respectively, in accordance with some embodiments of the disclosed subject matter. In some embodiments, focusing conjugate plane 80 can be determined mathematically based on characteristics of automatic focus system 100. In other embodiments, focusing conjugate plane 80 can be determined experimentally, for example, by generating a set of sharpness curves for one of offset focusing cameras 70 and 72 as described, for example, in 710-740.

After process 700 begins, at 710, specimen S can be placed on stage 30 and imaging device 5 can be used to determine and record when the relative Z position for when the specimen is in-focus, as discussed above in connection with FIG. 4. For example, FIG. 4 shows a specimen to be in focus at a relative Z position of 1500 µm (represented by line 130), which is at the peak of the curve shown in FIG. 4. Process 700 can find this relative Z position by stepping through any suitable number of Z positions in the range of Z positions shown by lines 137 and 142, capturing an image with imaging device 5 at each position, and determining a relative sharpness value (as described above). This highest of these sharpness values can be determined to correspond to the in-focus point.

At 720, offset focusing camera 70 can be moved incrementally in a horizontal direction and a sharpness curve, or a set of sharpness values relative to different relative Z positions, can be calculated at each horizontal position of the offset focusing camera. The position of the offset focusing camera where the peak of its sharpness curve, or the maximum sharpness value, occurs can be defined as being at the position at which focusing conjugate plan 80 lies as shown in FIG. 1. This position can be defined as being the in-focus relative Z position for camera 70 and can be recorded. In some embodiments, the maximum sharpness value at the in-focus relative Z position for camera 70 can be stored by control system 108 as the sharpness setpoint for automatic focus system 100, a particular specimen, specimen class and/or any other suitable classification group.

At 725, the in-focus relative Z position for camera 72 can be the same as the in-focus relative Z position for camera 70 (e.g., when focusing lenses 22 and 24 are the same). In such cases, camera 72 can be simply moved to the same in-focus relative Z position (which is at focusing conjugate plane 80) as camera 70.

In some embodiments, however, the in-focus relative Z position for camera 72 can be different from the in-focus relative Z position for camera 70. In such cases, offset focusing camera 72 can be moved incrementally in a horizontal direction and a sharpness curve, or a set of sharpness values relative to different relative Z positions, can be calculated at each horizontal position of the offset focusing camera. The position of the offset focusing camera where the peak of its sharpness curve, or the maximum sharpness value, occurs can be defined as being at the position at which a focusing conjugate plane lies (not shown in the figures). This position can be defined as being the in-focus relative Z position for camera 72 and can be recorded. In some embodiments, the maximum sharpness value at the in-focus relative Z position for camera 72 can be stored by control system 108 as the sharpness setpoint for camera 72.

While 720 discusses performing actions for camera 70 and 725 discusses performing actions for camera 72, the cameras for which action are taken in 70 and 72 can be swapped in some embodiments.

At 730, offset focusing camera 70 can be positioned at an offset distance f1 on a first side (e.g., positive, negative, left, right, top, bottom) of its in-focus relative Z position. Any suitable offset distance value can be used in some embodiments. For example, in some embodiments, offset focusing camera 70 can initially be positioned at 30 cm, 15 cm, 10 cm, and/or any other suitable offset distance from its in-focus relative Z position.

At 735, offset focusing camera 72 can be positioned at an offset distance f2 on a second, opposite side (e.g., negative, positive, right, left, bottom, top, respectively) of its in-focus relative Z position. That is, for example, if camera 70 is positioned on the left of its in-focus relative Z position, then camera 72 is positioned on the right side of its in-focus relative Z position, and vice versa. Any suitable offset distance value can be used in some embodiments. For example, in some embodiments, offset focusing camera 72 can initially be positioned at the same offset distance from its in-focus relative Z position as offset focusing camera 70 is from its in-focus relative Z position (e.g., 30 cm, 15 cm, 10 cm, and/or any other suitable offset distance from its in-focus relative Z position).

In some embodiments, the initial offset distances for f1 and f2 do not have to be equal to each other. The initial offset distances can be based on optical characteristics of automatic focus system 100 and/or precision requirements for focusing. The closer offset focusing camera 70 or 72 is placed to focusing conjugate plane 80, the steeper the slope of its sharpness curve at focusing conjugate plane 80. A steeper slope represents a larger change in sharpness versus a smaller change in Z height (also referred to as greater resolution). A steeper slope can be desirable because it allows for finer focal adjustment and control.

More specifically, if the range of Z movement (e.g., the distance between lines 137 and 142 shown in FIG. 6) is larger, then offset focusing cameras 70 and 72 can be positioned farther away from focusing conjugate plane 80 than if the range of Z movement is smaller.

In some embodiments, offset distances f1 and f2 can also be based on the steepness of the sharpness curve at the Z position where the specimen is in optimum focus for imaging device 5. For example, if the range of Z movement necessary to bring a specimen in focus is small (e.g., between 1300 µm-1700 µm), then offset focusing cameras 70 and 72 can be placed closer to focusing conjugate plane 80, because a closer position has a steeper slope and greater resolution compared to an offset distance farther away from focusing conjugate plane 80. In some embodiments, offset distances f1 and f2 farther away from focusing conjugate plane 80 can be selected to accommodate a maximum range of Z movement for automatic focus system 100, so that the offset focusing cameras 70 and 72 do not have to constantly be repositioned for specimens of varying thicknesses.

At 740, one of offset focusing cameras 70 and 72 can remain in a fixed position and the other offset focusing camera can be repositioned until the sharpness curves (e.g., sharpness curves A and B shown in FIG. 5) calculated for offset focusing cameras 70 and 72, respectively, intersect at focusing conjugate plane 80. For example, second focusing camera 72 can remain in a fixed position, offset from focusing conjugate plane 80, and a sharpness curve for specimen S, using second offset focusing camera 72, can be calculated and recorded. In particular, the sharpness value for specimen S (e.g., 28) at in-focus Z position 130 (e.g., 1500 μm), using offset focusing camera 72, can be recorded. Then first offset focusing camera 70 can be moved incrementally in a horizontal direction, towards or away from focusing conjugate plane 80 until it is determined that sharpness curve A intersects with sharpness curve B at in-focus Z position 130 (e.g., as shown in FIG. 5), which lies on focusing conjugate plane 80. The slopes will intersect when the sharpness value for a specimen at in-focus Z position 130, using first focusing camera 70, is the same value as using second offset focusing camera 72 (e.g., 28) at in-focus Z position 130. At the point of intersection, the slopes of sharpness curves A and B (i.e., any slope encompassing the point of intersection) are opposite to each other. Sharpness curve A can be calculated and recorded at the position of intersection. In some embodiments, the recorded sharpness curves A and B can be used to evaluate the relationship between different points on curves A and B (i.e., points other than the point of intersection) relative to focusing conjugate plane 80 and used to analyze a specimen or to set the focus at a plane other than the conjugate plane.

In some embodiment, the relative sharpness value at the intersection of curves A and B preferably do not occur at the very top or the very bottom of the sharpness curve. Rather, in some embodiments, the intersection can occur in any suitable range within the minimum and maximum values of the sharpness curves, such as between 10-90% of minimum and maximum values of the sharpness curves, between 5-95% of minimum and maximum values of the sharpness curves, between 20-80% of minimum and maximum values of the sharpness curves, etc.

In other embodiments, both offset focusing cameras 70 and 72 can be moved towards and/or away from focusing conjugate plane 80, until sharpness curve A intersects with curve B at in-focus Z position 130. Sharpness curves A and B can be calculated, for example, as described in connection with FIG. 4. The disclosed methods for calibrating offset distances f1 and f2 are just examples and are not intended to be limiting.

In some embodiments, sharpness curves do not need to be calculated for focusing cameras A and B to find offset distances f1 and f2. For example, one of offset focusing cameras 70 or 72 can be moved until the sharpness values calculated for images of a specimen captured by focusing cameras A and B at in-focus Z position 130 are equal.

In some embodiments, offset distances f1 and f2 can be set once for automatic focus system 100. In other embodiments, offset distances f1 and f2 can be recalibrated to accommodate different objectives, different specimen thicknesses, different specimen classes or any suitable criteria. For example, offset distances f1 and f2 can be decreased for higher magnification objectives to accommodate a smaller depth of field (focus) and smaller range of Z movement. In some embodiments, offset distances f1 and f2 can be saved by control system 108 as offset distance setpoints. The offset distance setpoints can be associated, for example, with the thickness and/or any other suitable characteristic of a specimen, the specimen class and/or any other suitable grouping of the specimen, and/or the optical characteristics of the microscope (e.g., the magnification of an objective). The offset distance setpoints can be used to automatically position offset focusing cameras 70 and 72.

In some embodiments, a specimen class can be defined based on specimens made from materials of similar reflective qualities.

The division of when the particular portions of process 700 are performed can vary, and no division or a different division is within the scope of the subject matter disclosed herein. Note that, in some embodiments, blocks of process 700 can be performed at any suitable times. It should be understood that at least some of the portions of process 700 described herein can be performed in any order or sequence not limited to the order and sequence shown in and described in the FIG. 7 in some embodiments. Also, some of the portions of process 700 described herein can be or performed substantially simultaneously where appropriate or in parallel in some embodiments. Additionally or alternatively, some portions of process 500 can be omitted in some embodiments.

Process 700 can be implemented in any suitable hardware and/or software. For example, in some embodiments, process 700 can be implemented in control system 108.

In some embodiments, control system 108 can collect data relating to the operation and/or configuration of auto focus system 100. For example, the data can include details regarding the configuration of auto focus system 100 when a specimen (or a portion of the specimen) is in-focus such as: the position of offset focusing cameras 70 and 72; the absolute position of: stage 30, objective 25, the top of the specimen on stage 30, and/or the distance between the top of stage 30 and objective 25; the sharpness setpoint, the position setpoint; the sharpness measurement used to determine that a specimen (or an area of a specimen) is in-focus.

Further, data relating to the operation of automatic focus, such as the time it took to achieve focus for each area of a specimen that is scanned, the number of images captured before a specimen (or an area of a specimen) was determined to be in focus, the total distance stage 30 and/or objective 25 had to travel to achieve focus, the recorded sharpness value. Data regarding the specimen, specimen class and/or any other suitable classification group can also be collected. The foregoing are just examples and are not intended to be limiting of the type of data that can be collected.

The data collected can further be analyzed by control system 108 and/or a remote computing device coupled to control system 108 to identify inefficiencies in the auto focus configuration and/or operation. Control system 108 and/or a remote computing device can further determine whether the inefficiencies detected correlate with an aspect of the configuration and/or operation of autofocus system 100 and make appropriate adjustments to the configuration and/or operation of autofocus system 100.

In some embodiments, any suitable artificial intelligence algorithm(s) can be used to identify inefficiencies and/or make suitable adjustments. For example, in some embodiments, the artificial intelligence algorithms can include one or more of the following, alone or in combination: machine learning; hidden Markov models; recurrent neural networks; convolutional neural networks; Bayesian symbolic methods; general adversarial networks; support vector machines; and/or any other suitable artificial intelligence.

Note that, in some embodiments, the techniques described herein for focusing a specimen can apply to focusing an entire specimen or to focusing just a portion of a specimen.

The provision of the examples described herein (as well as clauses phrased as "such as," "e.g.," "including," and the like) should not be interpreted as limiting the claimed subject matter to the specific examples; rather, the examples are intended to illustrate only some of many possible aspects. It should also be noted that, as used herein, the term mechanism can encompass hardware, software, firmware, or any suitable combination thereof.

Some portions of above description present the features of the present disclosure in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "determining," "displaying," or the like, refer to the action and processes of a computer system, or similar electronic computing device, that manipulates and transforms data represented as physical (electronic) quantities within the computer system memories or registers or other such information storage, transmission or display devices.

Certain aspects of the present disclosure include process steps and instructions described herein in the form of an algorithm. It should be noted that the process steps and instructions of the present disclosure could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of non-transient computer-readable storage medium suitable for storing electronic instructions. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein, and any references to specific languages are provided for disclosure of enablement and best mode of the present disclosure.

The automatic microscopic focus system and method have been described in detail with specific reference to these illustrated embodiments. It will be apparent, however, that various modifications and changes can be made within the spirit and scope of the disclosure as described in the foregoing specification, and such modifications and changes are to be considered equivalents and part of this disclosure. The scope of the invention is limited only by the claims that follow.

What is claimed is:

1. A system for automatically focusing a microscope, comprising:
   an objective;
   a stage for positioning a specimen on a first image forming conjugate plane;
   a first focusing camera, configured for focusing, positioned on a first side of a second image forming conjugate plane at a first offset distance;
   a second focusing camera, configured for focusing, positioned on a second side of the second image forming conjugate plane at a second offset distance;
   wherein the first offset distance and the second offset distance are determined so that sharpness measurements for images of the specimen captured by each of the first focusing camera and the second focusing camera, at a same distance between the objective and the stage, are equal at the second image forming conjugate plane;
   a primary illumination source;
   an imaging device positioned on a third image forming conjugate plane; and
   a hardware processor coupled to the first focusing camera and the second focusing camera that is configured to determine that the specimen is in focus when a sharpness value of the specimen using the first focusing camera is equal to a sharpness value of the specimen using the second focusing camera.

2. The system of claim 1, wherein the hardware processor is further configured to:
   measure a first sharpness value (SA1) of the specimen at a first position (Z1) of the stage relative to the objective using the first focusing camera;
   measure a second sharpness value (SB1) of the specimen at the first position (Z1) of the stage relative to the objective using the second focusing camera;
   measure a third sharpness value (SA2) of the specimen at a second position (Z2) of the stage relative to the objective using the first focusing camera;
   measure a fourth sharpness value (SB2) of the specimen at the second position (Z2) of the stage relative to the objective using the second focusing camera;
   calculate a first slope equal to (SA2−SA1)/(Z2−Z1);
   calculate a second slope equal to (SB2−SB1)/(Z2−Z1); and
   adjust a distance between the objective and the stage to a third position so that a fifth sharpness value (SA3) measured for the specimen using the first focusing camera is equal to a sixth sharpness value (SB3) measured for the specimen using the second focusing camera.

3. The system of claim 1, further comprising:
   a secondary illumination source;
   wherein the primary illumination source is configured to emit light in a first wavelength range that is received by the imaging device; and
   wherein the secondary illumination source is configured to emit light in a second wavelength range which is different from the first wavelength range and that projects light through a focusing pattern that is positioned on a fourth image forming conjugate plane that is received by the first focusing camera and the second focusing camera.

4. The system of claim 3, wherein the hardware processor is further configured to:
adjust a distance between the objective and the stage to a fourth position (Z4) and measure a seventh sharpness value (SA4) of the specimen using the first focusing camera and an eighth sharpness value (SB4) of the specimen using the second focusing camera;
calculate a third slope equal to (SA4−SA3)/(Z4−Z3);
calculate a fourth slope equal to (SB4−SB3)/(Z4−Z3);
determine if a direction of the third slope and a direction of the second slope are opposite; and
when the direction of the third slope and the direction of the second slope are not opposite, continue to adjust the distance between the objective and the stage so that a ninth sharpness value measured for the specimen using the first focusing camera is equal to a tenth sharpness value measured for the specimen using the second focusing camera.

5. The system of claim 3, further comprising:
a first filter positioned in an optical path between the secondary illumination source and the imaging device to prevent light from the secondary illumination source from reaching the imaging device; and
a second filter positioned in an optical path between the first illumination source and the first focusing camera and the second focusing camera to prevent light from the primary illumination source from reaching the first focusing camera and the second focusing camera.

6. The system of claim 3, wherein the hardware processor is further configured to:
measure a first sharpness value (SA1) of the specimen at a first position (Z1) of the stage relative to the objective using the first focusing camera;
measure a second sharpness value (SB1) of the specimen at the first position (Z1) of the stage relative to the objective using the second focusing camera;
measure a third sharpness value (SA2) of the specimen at a second position (Z2) of the stage relative to the objective using the first focusing camera;
measure a fourth sharpness value (SB2) of the specimen at the second position (Z2) of the stage relative to the objective using the second focusing camera;
calculate a first slope equal to (SA2−SA1)/(Z2−Z1);
calculate a second slope equal to (SB2−SB1)/(Z2−Z1); and
adjust a distance between the objective and the stage to a third position so that a fifth sharpness value (SA3) measured for the specimen using the first focusing camera is equal to a sixth sharpness value (SB3) measured for the specimen using the second focusing camera.

7. The system of claim 6, wherein the hardware processor is further configured to:
adjust a distance between the objective and the stage to a fourth position (Z4) and measure a seventh sharpness value (SA4) of the specimen using the first focusing camera and an eighth sharpness value (SB4) of the specimen using the second focusing camera;
calculate a third slope equal to (SA4−SA3)/(Z4−Z3);
calculate a fourth slope equal to (SB4−SB3)/(Z4−Z3);
determine if a direction of the third slope and a direction of the second slope are opposite; and
when the direction of the third slope and the direction of the second slope are not opposite, continue to adjust the distance between the objective and the stage so that a ninth sharpness value measured for the specimen using the first focusing camera is equal to a tenth sharpness value measured for the specimen using the second focusing camera.

8. The system of claim 1, wherein the imaging device is configured for taking images of the specimen when the specimen is determined to be in focus by the first focusing camera and the second focusing camera.

9. The system of claim 1, wherein the hardware processor is further configured to cause at least one of the stage and the objective to be moved to achieve a coarse focus and a fine focus.

10. The system of claim 1, wherein the hardware processor is further configured to save at least one of a position of the stage relative to the objective, an absolute position of the stage, and an absolute position of the objective.

11. A method for automatically focusing a microscope having at least an objective, a stage for positioning a specimen on a first image forming conjugate plane, a first focusing camera, configured for focusing, positioned on a first side of a second image forming conjugate plane at a first offset distance, a second focusing camera, configured for focusing, positioned on a second side of the second image forming conjugate plane at a second offset distance, a primary illumination source, an imaging device positioned on a third image forming conjugate plane, the method comprising:
setting the first offset distance and the second offset distance so that sharpness measurements for images of the specimen captured by each of the first focusing camera and the second focusing camera, at a same distance between the objective and the stage, are equal at the second image forming conjugate plane; and
determining that the specimen is in focus when a sharpness value of the specimen using the first focusing camera is equal to a sharpness value of the specimen using the second focusing camera.

12. The method of claim 11, further comprising:
measuring a first sharpness value (SA1) of the specimen at a first position (Z1) of the stage relative to the objective using the first focusing camera;
measuring a second sharpness value (SB1) of the specimen at the first position (Z1) of the stage relative to the objective using the second focusing camera;
measuring a third sharpness value (SA2) of the specimen at a second position (Z2) of the stage relative to the objective using the first focusing camera;
measuring a fourth sharpness value (SB2) of the specimen at the second position (Z2) of the stage relative to the objective using the second focusing camera;
calculating a first slope equal to (SA2−SA1)/(Z2−Z1);
calculating a second slope equal to (SB2−SB1)/(Z2−Z1); and
adjusting a distance between the objective and the stage to a third position so that a fifth sharpness value (SA3) measured for the specimen using the first focusing camera is equal to a sixth sharpness value (SB3) measured for the specimen using the second focusing camera.

13. The method of claim 11, wherein the microscope also has a secondary illumination source; wherein the primary illumination source is configured to emit light in a first wavelength range that is received by the imaging device; and wherein the secondary illumination source is configured to emit light in a second wavelength range which is different from the first wavelength range and that projects light through a focusing pattern that is positioned on a fourth image forming conjugate plane that is received by the first focusing camera and the second focusing camera.

14. The method of claim 13, further comprising:
adjusting a distance between the objective and the stage to a fourth position (Z4) and measure a seventh sharpness value (SA4) of the specimen using the first focusing camera and an eighth sharpness value (SB4) of the specimen using the second focusing camera;
calculating a third slope equal to (SA4−SA3)/(Z4−Z3);
calculating a fourth slope equal to (SB4−SB3)/(Z4−Z3);
determining if a direction of the third slope and a direction of the second slope are opposite; and
when the direction of the third slope and the direction of the second slope are not opposite, continuing to adjust the distance between the objective and the stage so that a ninth sharpness value measured for the specimen using the first focusing camera is equal to a tenth sharpness value measured for the specimen using the second focusing camera.

15. The method of claim 13, wherein the microscope also has a first filter positioned in an optical path between the secondary illumination source and the imaging device to prevent light from the secondary illumination source from reaching the imaging device; and a second filter positioned in an optical path between the first illumination source and the first focusing camera and the second focusing camera to prevent light from the primary illumination source from reaching the first focusing camera and the second focusing camera.

16. The method of claim 13, further comprising:
measuring a first sharpness value (SA1) of the specimen at a first position (Z1) of the stage relative to the objective using the first focusing camera;
measuring a second sharpness value (SB1) of the specimen at the first position (Z1) of the stage relative to the objective using the second focusing camera;
measuring a third sharpness value (SA2) of the specimen at a second position (Z2) of the stage relative to the objective using the first focusing camera;
measuring a fourth sharpness value (SB2) of the specimen at the second position (Z2) of the stage relative to the objective using the second focusing camera;
calculating a first slope equal to (SA2−SA1)/(Z2−Z1);
calculating a second slope equal to (SB2−SB1)/(Z2−Z1); and
adjusting a distance between the objective and the stage to a third position so that a fifth sharpness value (SA3) measured for the specimen using the first focusing camera is equal to a sixth sharpness value (SB3) measured for the specimen using the second focusing camera.

17. The method of claim 16, further comprising:
adjusting a distance between the objective and the stage to a fourth position (Z4) and measure a seventh sharpness value (SA4) of the specimen using the first focusing camera and an eighth sharpness value (SB4) of the specimen using the second focusing camera;
calculating a third slope equal to (SA4−SA3)/(Z4−Z3);
calculating a fourth slope equal to (SB4−SB3)/(Z4−Z3);
determining if a direction of the third slope and a direction of the second slope are opposite; and
when the direction of the third slope and the direction of the second slope are not opposite, continuing to adjust the distance between the objective and the stage so that a ninth sharpness value measured for the specimen using the first focusing camera is equal to a tenth sharpness value measured for the specimen using the second focusing camera.

18. The method of claim 11, wherein the imaging device is configured for taking images of the specimen when the specimen is determined to be in focus by the first focusing camera and the second focusing camera.

19. The method of claim 11, further comprising causing at least one of the stage and the objective to be moved to achieve a coarse focus and a fine focus.

20. The method of claim 11, saving at least one of a position of the stage relative to the objective, an absolute position of the stage, and an absolute position of the objective.

* * * * *